[19] United States Patent
Shoji et al.

[11] Patent Number: 5,459,257
[45] Date of Patent: Oct. 17, 1995

[54] SULFATED OLIGOGLYCOSIDE ACYLATE AND ANTIVIRAL AGENT CONTAINING THE SAME AS ACTIVE INGREDIENT

[75] Inventors: Tadao Shoji, Sakura; Akira Kasai, Matsudo; Osamu Misumi; Naoya Ikushima, both of Sakura; Naoki Yamamoto, Tokyo; Hideki Nakashima; Kazuhiko Inazawa, both of Yamanashi; Nahoko Takahashi, Chiba, all of Japan

[73] Assignee: Dainippon Ink and Chemicals, Inc., Tokyo, Japan

[21] Appl. No.: 179,623

[22] Filed: Jan. 7, 1994

[30] Foreign Application Priority Data

Jan. 11, 1993 [JP] Japan ................... 5-002566

[51] Int. Cl.⁶ .................. C07H 13/12; C07H 11/00
[52] U.S. Cl. .................. 536/118; 536/115; 536/116; 536/123.1
[58] Field of Search .................. 514/54, 56, 59, 514/12, 885; 536/118, 21, 53, 54, 115, 116, 123.1

[56] References Cited

U.S. PATENT DOCUMENTS

| | | | |
|---|---|---|---|
| 3,478,016 | 11/1969 | Rowley | 514/53 |
| 4,597,770 | 7/1986 | Forand et al. | 44/280 |
| 4,761,401 | 8/1988 | Couchman et al. | 514/53 |
| 4,783,446 | 11/1988 | Neushul | 514/54 |
| 4,840,815 | 6/1989 | Meyer et al. | 426/611 |
| 4,840,941 | 6/1989 | Veno et al. | 514/59 |
| 5,100,573 | 3/1992 | Balzer | 252/174.17 |
| 5,272,261 | 12/1993 | Cardin et al. | 536/21 |
| 5,280,111 | 1/1994 | Shoji et al. | 536/4.1 |
| 5,288,704 | 2/1994 | Ungheri et al. | 514/12 |
| 5,298,488 | 3/1994 | Kojima et al. | 514/8 |

FOREIGN PATENT DOCUMENTS

| | | |
|---|---|---|
| 0497988 | 8/1992 | European Pat. Off. . |
| 0506048 | 9/1992 | European Pat. Off. . |
| 0532026 | 3/1993 | European Pat. Off. . |
| 3921761 | 1/1991 | Germany . |
| 3-43401 | 2/1991 | Japan . |
| 4-264102 | 9/1992 | Japan . |
| 9213541 | 8/1992 | WIPO . |

OTHER PUBLICATIONS

M. Baba et al., Journal of Acquired Immune Deficiency Syndromes, 3(5), pp. 493–499 (1990).

Primary Examiner—Douglas W. Robinson
Assistant Examiner—Howard C. Lee
Attorney, Agent, or Firm—Armstrong, Westerman, Hattori, McLeland & Naughton

[57] ABSTRACT

A sulfated oligoglycoside acylate comprising monosaccharides of a single or two kinds as the constituents, wherein the hydrogen in the hydroxyl group at the 1-position of a reducing end sugar of the oligosaccharide formed via the glycoside bond of these monosaccharides has been substituted with an aglycon selected from a group consisting of alkyl groups, aromatic alkyl groups, aromatic alkoxy groups and tocopheryl groups; from 12 to 80% of the residual hydroxyl groups have been acylated with an acyl group selected from a group consisting of aliphatic acyl groups and aromatic acyl groups; and 88 to 20% thereof have been sulfated; or a physiologically acceptable salt thereof provided that compounds wherein the aglycon is an alkyl group and the acyl group is an aliphatic acyl group are excluded is disclosed. Further, an antiviral agent, which exerts a long-lasting antiviral action particularly on HIV, containing said compound as an active ingredient is disclosed.

21 Claims, No Drawings

SULFATED OLIGOGLYCOSIDE ACYLATE AND ANTIVIRAL AGENT CONTAINING THE SAME AS ACTIVE INGREDIENT

FIELD OF THE INVENTION

This invention relates to a sulfated oligoglycoside acylate having an antiviral activity and an antiviral agent containing this compound as an antiviral ingredient.

BACKGROUND OF THE INVENTION

Known antiviral agents comprising glycosides of sulfated oligosaccharides include EP 0497988, EP 0506048 and EP 0532026 which have been each provided by the present inventors. It has been clarified that when a sulfated oligosaccharide is formulated into a glycoside, its antiviral activity is increased one order over the activity of the non-glycoside compound. When orally administered, however, these sulfated compounds, which have never been acylated at the sugar hydroxyl groups, are poor in long-lasting action in the blood.

Although antiviral agents comprising sulfated polysaccharide alkyl ethers or alkyl esters have been disclosed in JP-A-3-43401, neither any aromatic glycosides, tocopherol glycosides nor aromatic esterification are described therein (the term "JP-A" as used herein means an "unexamined published Japanese patent application").

Although U.S. Pat. No. 4,840,815 has disclosed esterified alkyl glycosides comprising oligosaccharides, these compounds are not sulfated but only esterified. Further, JP-A-4-264102 has disclosed compounds wherein the sugar hydroxyl groups of galactomannane are substituted with aliphatic, aromatic/aliphatic or aromatic ethers or aromatic esters. However, these compounds are neither glycosides nor sulfated compounds, different from the compounds of the present invention.

U.S. Pat. No. 4,597,770 has disclosed sulfates of alkyl glycoside alkyl ethers comprising mono- to deca-saccharides as a coal-slurrying agent. However, the detailed structures of these compounds are not clearly given therein and the sugar hydroxyl groups of these compounds have never been acylated. Thus the compounds disclosed in this patent completely differ from the compounds according to the present invention.

Furthermore, U.S. Pat. No. 4,761,401 has disclosed diglycoside sulfates containing uronic acid. However, these compounds also differ from the compounds according to the present invention, since their sugar chains consist of two saccharides and these compounds contain uronic acid. Although U.S. Pat. No. 3,478,016 has disclosed sulfates of cellulose esters and cellulose ethers, these compounds are not intended to be used as an antiviral agent and, further, their structures have not been clearly given in this patent.

As described above in brief, there has been known no oligoglycoside the sugar hydroxyl group of which has been acylated and sulfated.

In recent years, there has been reported that sulfated polysaccharides are effective as an antiviral agent, in particular, an anti-HIV agent [refer to U.S. Pat. No. 4,783,446 and M. Baba et al., Journal of Acquired Immune Deficiency Syndrome, 3, 493–499 (1990)]. However, each of these sulfated polysaccharides has no glycoside structure and a large molecular weight of several ten thousands or above, which causes various problems such as having poor absorption characteristics in vivo, being hardly usable in oral administration, having a high anticoagulant activity and frequently metabolising within 1 hour after the administration due to a poor long-lasting action in the blood. In addition, AZT (3'-azido-3'-deoxythymidine), which has been widely used as an anti-AIDS agent, has serious side effects. Accordingly, it has been urgently required to develop a novel drug with a low toxicity.

SUMMARY OF THE INVENTION

It is an object of the present invention to provide a drug which has a low toxicity and an excellent long-lasting action in the blood and, in particular, shows an excellent long-lasting activity when administered orally.

In order to provide an excellent antiviral agent, the present inventors have conducted extensive studies. As a result, they have successfully found out that novel sulfated oligoglycoside acylates and physiologically acceptable salts thereof are usable as a highly safe drug, since they are less toxic and yet excellent in the long-lasting antiviral activity in the blood even in oral administration and have a low anticoagulant activity, different from sulfated polysaccharides. The present invention has been completed on the basis of this finding.

Accordingly, the present invention relates to a sulfated oligoglycoside acylate comprising monosaccharides of a single or two kinds as the constituents, wherein the hydrogen in the hydroxyl group at the 1-position of a reducing end sugar of the oligosaccharide formed via the glycoside bond of these monosaccharides has been substituted with an aglycon selected from a group consisting of alkyl groups, aromatic alkyl groups, aromatic alkoxy groups and tocopheryl groups, from 12 to 80% of the residual hydroxyl groups have been acylated with an acyl group selected from a group consisting of aliphatic acyl groups and aromatic acyl groups, and 88 to 20% thereof have been sulfated, or a physiologically acceptable salt thereof provided that compounds wherein the aglycon is an alkyl group and the acyl group is an aliphatic acyl group are excluded and an antiviral agent containing the same as an active ingredient.

DETAILED DESCRIPTION OF THE INVENTION

Now, the compound of the present invention will be described in greater detail.

In the compound of the present invention, the number of monosaccharides constituting the oligosaccharide, namely, the length of the sugar chain varies depending on the employed saccharides, aglicon or the like. For using as an antiviral agent, a sugar chain consisting of 3 or more saccharides are preferable. From the viewpoints of anticoagulant activity and biocompatibility, on the other hand, a sugar chain consisting of not more than 20 saccharides are usually preferable. That is to say, sugar chains consisting of 3 to 20 saccharides are preferable and those consisting of 3 to 12 saccharides are still preferable.

The oligosaccharide moiety of the compound of the present invention comprises monosaccharides of a single or two kinds as the constituents. Although various monosaccharides are usable therefor, it is preferable to use those selected from among glucose, galactose, mannose, talose, idose, altrose, allose, gulose, xylose, arabinose, rhamnose, fucose, fructose, ribose and deoxyribose. Also, monosaccharides having amino groups such as glucosamine and galactosamine may be used therefor.

From the viewpoint of antiviral activity, the glycoside bond between the monosaccharides in the compound of the present invention may be either a (1→2), (1→3), (1→4), (1→5) or (1→6) bond and the binding manner may be either α- or β-binding. Also, branched sugar chains are usable. Among all, saccharides with β(1→3), β(1→4), α(1→4) and α(1→6) bonds are particularly preferable. In order to maintain the long-lasting activity when administered as a drug, in particular, β(1→3) saccharides and β(1→4) saccharides are highly usable. For example, it is preferable to use laminari-oligoglucose (i.e., oligosaccharides formed through a β-bond between the 3-position of a glucose unit and the 1-position of the subsequent glucose unit), namely, oligosaccharides obtained by decomposing polysaccharides such as curdlan and laminaran, oligosaccharides wherein the 4-position of the galactose site in lactose forms a β-bond together with the 1-position of galactose and galactose units subsequently form β(1→4) bonds together with the 4-position of the terminal galactose of oligosaccharide, and oligosaccharides wherein glucose forms an α(1→4) bond such as malto-oligoglucose. Further, isomalto-oligoglucose [glucose α(1→6) binding oligosaccharides] are usable therefor. Furthermore, mannose-series oligosaccharides, β(1→6) oligoglucose, xylan-series oligosaccharides, schizopylan-series oligosaccharides, lentinan-series oigosaccharides, galactan-series oligosaccharides and pullulan-series oligosaccharides may be used therefor. Furthermore, some of the hydroxyl groups of these oligosaccharides may be replaced by amino groups or substituted amino groups.

It is necessary that the compound of the present invention has been substituted at the hydroxyl group at the 1-position of the reducing end of the oligosaccharide with an aglycon. As examples of the aglycon, alkyl groups, aromatic alkyl groups, aromatic alkoxy groups and tocopheryl groups may be cited.

As the alkyl groups, straight-chain or branched alkyl groups having 1 to 24, preferably 4 to 22 and still preferably 8 to 12, carbon atoms may be cited. These alkyl groups may involve unsaturated bonds. Examples thereof include methyl, ethyl, propyl, isopropyl, butyl, isobutyl, tert-butyl, pentyl, isopentyl, 2-methylbutyl, hexyl, heptyl, octyl, 2-octyl, 2-ethylhexyl, 2,2,3,3-tetramethylbutyl, nonyl, decyl, undecyl, dodecyl, tetradecyl, hexadecyl, octadecyl, eicosyl, docosyl and tricosyl groups.

As the aromatic alkyl groups, phenyl groups substituted with straight-chain or branched alkyl groups having 1 to 18, preferably 4 to 12, carbon atoms may be cited. The alkyl groups serving as substituents may involve unsaturated bonds. Examples thereof include o-methylphenyl, p-methylphenyl, m-methylphenyl, ethylphenyl, propylphenyl, butylphenyl, pentylphenyl, hexylphenyl, heptylphenyl, octylphenyl, nonylphenyl, decylphenyl, dodecylphenyl, tetradecylphenyl, hexadecylphenyl, octadecylphenyl, eicosylphenyl and tricosylphenyl groups.

As the aromatic alkoxy groups, phenyl groups substituted with straight-chain or branched alkoxy groups having 1 to 18, preferably 4 to 12, carbon atoms may be cited. The alkoxy groups serving as susbstituents may involve unsaturated bonds. Examples thereof include methoxyphenyl, ethoxyphenyl, propoxyphenyl, butoxyphenyl, pentyloxyphenyl, hexyloxyphenyl, heptyloxyphenyl, octyloxyphenyl, nonyloxyphenyl, decyloxyphenyl, dodecyloxyphenyl, tetradecyloxyphenyl, hexadecyloxyphenyl, octadecyloxyphenyl, eicosyloxyphenyl and tricosyloxyphenyl groups.

The tocopheryl groups may be either dl-, d- or l-form. Further, each of α, β, γ, δ, ε, ζ and η-tocopheryl groups may be used. In the compound according to the present invention, from 12 to 80% of the sugar hydroxyl groups in the oligoglycoside compound having an aglycon have been acylated with an aromatic acyl group (in the case where the aglycon is an alkyl group) or an aliphatic acyl group or an aromatic acyl group (in the case where the aglycon is an aromatic alkyl group, an aromatic alkoxy group or a tocopheryl group). The locations of the acylated hydroxyl groups may be arbitrarily determined except the hydroxyl group at the 1-position of the reducing end sugar.

As the aliphatic acyl groups, straight-chain or branched alkanoyl groups having 2 to 24, preferably 3 to 22 and still preferably 4 to 12, carbon atoms may be cited. Examples thereof include acetyl, propionyl, butyryl, pentanoyl, hexanoyl, heptanoyl, octanoyl, decanoyl, dodecanoyl, hexadecanoyl, eicosanoyl, docosanoyl and tricosanoyl groups.

As the aromatic acyl groups, an unsubstituted benzoyl group and benzoyl groups substituted with alkyl groups, alkoxy groups or halogen atoms may be cited. As the alkyl and alkoxy groups, those having 1 to 18, preferably 3 to 12, carbon atoms may be cited. As the halogen atoms, fluorine, chlorine, bromine and iodine atoms may be cited. The number and locations of these substituents may be arbitrarily selected. Examples thereof include benzoyl, fluorobenzoyl, 2,4-difluorobenzoyl, chlorobenzoyl, 4-methylbenzoyl, 4-butylbenzoyl, 4-pentylbenzoyl, 4-hexylbenzoyl, 4-octylbenzoyl, 4-propoxybenzoyl, 4-butoxybenzoyl, 4-pentoxybenzoyl and 4-dodecyloxybenzoyl groups, though the present invention is not restricted thereto.

After the completion of the acylation, the hydroxyl groups remaining unreacted are sulfated. Thus the target compound of the present invention can be obtained. As the counter ion to the sulfate, any physiologically acceptable cations may be used. For example, the target compound can be finally taken out in the form of a salt commonly employed in the art, for example, sodium salt, potassium salt or magnesium salt. Also, hydrogen ion may be present therein as the counter ion to the sulfate.

The percent of the sulfate groups ranges from 20 to 88% of the sugar hydroxyl groups. The sulfated site may be arbitrarily selected, excluding the 1-position of the reducing end and the acylated hydroxyl groups. A higher percentage of the sulfate groups is the more desirable.

The percent of the acyl groups and the percent of the sulfate groups in the sulfated oligoglycoside acylate of the present invention can be calculated in the following manner.

For example, an oligoglycoside consisting of 5 galactose units involves 16 hydroxyl groups which can be acylated. Suppose that 4 of these hydroxyl groups are acylated, $$4/16 \times 100 = 25 \ (\%).$$

Thus 25% of the hydroxyl groups have been acylated. That is to say, the percent of the acyl groups is 25%. Subsequently, 8 of the remaining hydroxyl groups in the acylated oligoglycoside are sulfated, $$8/16 \times 100 = 50 \ (\%).$$

Thus the percent of the sulfate groups is 50%.

Regarding the percents of the sulfate groups and acyl groups to the hydroxyl groups in the oligoglycoside, a higher percent of the sulfate groups is the more desirable from the viewpoint of the antiviral action and a higher percent of the acyl groups is the more desirable in order to improve the oral absorption characteristics. Accordingly, the percents of the sulfate groups and the acyl groups can be varied depending on the utilization conditions. When the compound of the present invention is to be intravenously administered, for example, it is recommended that the percent of the acyl groups is suppressed while the percent of the sulfate groups is elevated. When it is to be orally administered, on the other hand, it is recommended to elevate the percent of the acyl groups. From the viewpoint of the antiviral activity, the percent of the sulfate groups is preferably not less than 20% to the hydroxyl groups in the oligoglycoside.

Namely, the percent of the acyl groups preferably ranges from 12 to 80%, still preferably from 30 to 60%, based on the hydroxyl groups in the glycoside, while the percent of the sulfate groups preferably ranges from 88 to 20%, still preferably from 70 to 40%, based on the hydroxyl groups in the glycoside.

The percents of the acyl groups and sulfate groups of the sulfated oligoglycoside acylate thus produced correspond to the values of a synthetic product formed via a single reaction. It is needless to say that each of these values therefore means the average of the synthesized molecules.

Now a general method for producing the compound of the present invention will be briefly described. However, it is to be understood that this method is not the one and only.

(1) Production of oligoglycoside

An oligosaccharide is treated with acetic anhydride in the presence of sodium acetate by a conventional method to thereby acetylate all hydroxyl groups in the target saccharide. Thus a peracetate is obtained. Next, an acid catalyst such as a Lewis acid (for example, zinc chloride, boron trifluoride etherate, stannic chloride, titanium tetrachloride, ferric chloride, trimethylsilyl triflate) or a protic acid (for example, sulfuric acid, p-toluenesulfonic acid) is used at a ratio of 0.1 to 1.5 mol per mol of the peracetate. In the presence of this acid catalyst, the above-mentioned peracetate is reacted with an alcohol or a phenol to be used as an aglycon in an aprotic solvent (for example, methylene chloride, toluene, xylene, dimethoxyethane) at a temperature ranging from $-30°$ C. to the boiling point of the employed solvent for 0.5 to 10 hours. After the completion of the reaction, the reaction mixture is after-treated in a conventional manner and purified by silica gel column chromatography. Thus a glycoside can be obtained. Although the anomeric ratio of the glycoside varies depending on the reaction conditions, the β-compound is mainly obtained. The ratio of the α-anomer to the β-anomer can be adjusted by controlling the production method, the selection of the catalyst and the purification procedure. As a matter of course, the subsequent reactions can be carried out without any problem even though the obtained product is the α-anomer. The glycoside peracetylate thus obtained can be deacetylated in a conventional manner, for example, by treating with sodium ethoxide in methanol at a reaction temperature ranging from room temperature to 50° C. Thus the target glycoside can be obtained.

(2) Production of oligoglycoside acylate

The glycoside obtained in the above (1) is acylated by a conventional method. For example, it is acylated by treating with an acyl halide in the presence of an amine at a temperature of from 0° C. to room temperature (esterification) or by treating with a carboxylic acid in the presence of a dehydrating agent (dehydration and esterification). The acylating agent may be used in an amount almost equivalent to the hydroxyl groups in the starting material, by taking the desired percent of the acyl groups into consideration. The percent of the acyl groups in the acylate thus obtained can be easily determined by analyzing the reaction product by nuclear magnetic resonance spectral analysis.

(3) Production of sulfated oligoglycoside acylate

The acylate obtained in the above (2) is sulfated by a conventional method employed for esterifying sugar hydroxyl groups. For example, the acylate is reacted with a sulfating agent, which has been selected depending on the desired percent of the sulfate groups, in an aprotic polar solvent such as dimethylformamide, pyridine or dimethylsulfoxide. This sulfating agent may be used in an amount of 1.0 to 3.0 equivalents, preferably 1.2 to 2.0 equivalents, to the hydroxyl groups contained in the starting material. As the sulfating agent, sulfur trioxide amine complexes such as sulfur trioxide pyridine complex or sulfur trioxide triethylamine complex may be used. The sulfation is performed by stirring in an inert gas at a temperature falling within a range of from room temperature to 90° C., preferably at 40° to 90° C., for 1 to 24 hours. After the completion of the reaction, the reaction product can be taken out in the form of a metal salt with the use of a metal hydroxide, an ion exchange resin or the like. The target product thus obtained can be purified by, for example, ion exchange membrane method, ion exchange column chromatography, reverse osmosis filtration, ultrafiltration or reprecipitation.

Now, typical examples of the sulfated oligoglycoside acylate, namely, the compound of the present invention will be given. However it is to be understood that the present invention is not restricted thereto.

Although each acyl group in the acylates in the following compound is expressed merely in the name of the acyl group, it means a compound of a percent of acyl groups of 12 to 80%. Similarly, each sulfate is expressed merely as a sulfated compound, though it means a compound of a percent of sulfate groups of 20 to 88%. Although counter ions are omitted, physiologically acceptable salts are involved in these compounds. Regarding sugar chains, a β(1→3) binding oligosaccharide of glucose is conventionally called a laminari-oligosaccharide and a laminaripentaoside means a laminari-oligosaccharide having a sugar chain consisting of 5 saccharides. Further, an β(1→4) binding oligosaccharide of glucose is conventionally called a malto-oligosaccharide and a maltopentaoside means a malto-oligosaccharide having a sugar chain consisting of 5 saccharides. Furthermore, an α(1→6) binding oligosaccharide of glucose is conventionally called an isomalto-oligosaccharide and an isomaltopentaoside means an isomalto-oligosaccharide having a sugar chain consisting of 5 saccharides.

Sulfated n-dodecyl O-benzoyl-laminaripentaoside
Sulfated n-dodecyl O-p-fluorobenzoyl-laminaripentaoside
Sulfated n-dodecyl O-2,4-di-fluorobenzoyl-laminaripentaoside
Sulfated n-dodecyl O-methylbenzoyl-laminaripentaoside
Sulfated n-dodecyl O-pentylbenzoyl-laminaripentaoside
Sulfated n-dodecyl O-octylbenzoyl-laminaripentaoside
Sulfated n-dodecyl O-dodecylbenzoyl-laminaripentaoside
Sulfated butylphenyl O-benzoyl-laminaripentaoside
Sulfated butylphenyl O-p-fluorobenzoyl-laminaripentaoside
Sulfated butylphenyl O-2,4-di-fluorobenzoyl-laminaripentaoside
Sulfated butylphenyl O-methylbenzoyl-laminaripentaoside
Sulfated butylphenyl O-pentylbenzoyl-laminaripentaoside
Sulfated butylphenyl O-octylbenzoyl-laminaripentaoside
Sulfated butylphenyl O-dodecylbenzoyl-laminaripentaoside
Sulfated butylphenyl O-acetyl-laminaripentaoside
Sulfated butylphenyl O-propionyl-laminaripentaoside
Sulfated butylphenyl O-butyryl-laminaripentaoside
Sulfated butylphenyl O-pentanoyl-laminaripentaoside
Sulfated butylphenyl O-hexanoyl-laminaripentaoside
Sulfated butylphenyl O-octanoyl-laminaripentaoside
Sulfated butylphenyl O-hexadecanoyl-laminaripentaoside Sulfated butylphenyl O-docosanoyl-laminaripentaoside
Sulfated heptylphenyl O-benzoyl-laminaripentaoside
Sulfated heptylphenyl O-p-fluorobenzoyl-laminaripentaoside
Sulfated heptylphenyl O-2,4-di-fluorobenzoyl-laminaripentaoside
Sulfated heptylphenyl O-methylbenzoyl-laminaripentaoside
Sulfated heptylphenyl O-pentylbenzoyl-laminaripentaoside
Sulfated heptylphenyl O-octylbenzoyl-laminaripentaoside
Sulfated heptylphenyl O-dodecylbenzoyl-laminaripentaoside
Sulfated heptylphenyl O-acetyl-laminaripentaoside
Sulfated heptylphenyl O-propionyl-laminaripentaoside
Sulfated heptylphenyl O-butyryl-laminaripentaoside
Sulfated heptylphenyl O-pentanoyl-laminaripentaoside
Sulfated heptylphenyl O-hexanoyl-laminaripentaoside
Sulfated heptylphenyl O-octanoyl-laminaripentaoside
Sulfated heptylphenyl O-hexadecanoyl-laminaripentaoside
Sulfated heptylphenyl O-docosanoyl-laminaripentaoside
Sulfated octylphenyl O-benzoyl-laminaripentaoside
Sulfated octylphenyl O-p-fluorobenzoyl-laminaripentaoside
Sulfated octylphenyl O-2,4-di-fluorobenzoyl-laminaripentaoside
Sulfated octylphenyl O-methylbenzoyl-laminaripentaoside
Sulfated octylphenyl O-pentylbenzoyl-laminaripentaoside
Sulfated octylphenyl O-octylbenzoyl-laminaripentaoside
Sulfated octylphenyl O-dodecylbenzoyl-laminaripentaoside
Sulfated octylphenyl O-acetyl-laminaripentaoside
Sulfated octylphenyl O-propionyl-laminaripentaoside
Sulfated octylphenyl O-butyryl-laminaripentaoside
Sulfated octylphenyl O-pentanoyl-laminaripentaoside
Sulfated octylphenyl O-hexanoyl-laminaripentaoside
Sulfated octylphenyl O-octanoyl-laminaripentaoside
Sulfated octylphenyl O-hexadecanoyl-laminaripentaoside
Sulfated octylphenyl O-docosanoyl-laminaripentaoside
Sulfated methoxyphenyl O-benzoyl-laminaripentaoside
Sulfated methoxyphenyl O-p-fluorobenzoyl-laminaripentaoside
Sulfated methoxyphenyl O-2,4-di-fluorobenzoyl-laminaripentaoside
Sulfated methoxyphenyl O-methylbenzoyl-laminaripentaoside
Sulfated methoxyphenyl O-pentylbenzoyl-laminaripentaoside
Sulfated methoxyphenyl O-octylbenzoyl-laminaripentaoside
Sulfated methoxyphenyl O-dodecylbenzoyl-laminaripentaoside
Sulfated methoxyphenyl O-acetyl-laminaripentaoside
Sulfated methoxyphenyl O-propionyl-laminaripentaoside
Sulfated methoxyphenyl O-butyryl-laminaripentaoside
Sulfated methoxyphenyl O-pentanoyl-laminaripentaoside
Sulfated methoxyphenyl O-hexanoyl-laminaripentaoside
Sulfated methoxyphenyl O-octanoyl-laminaripentaoside
Sulfated methoxyphenyl O-hexadecanoyl-laminaripentaoside
Sulfated methoxyphenyl O-docosanoyl-laminaripentaoside
Sulfated butoxyphenyl O-benzoyl-laminaripentaoside
Sulfated butoxyphenyl O-p-fluorobenzoyl-laminaripentaoside
Sulfated butoxyphenyl O-2,4-di-fluorobenzoyl-laminaripentaoside
Sulfated butoxyphenyl O-methylbenzoyl-laminaripentaoside
Sulfated butoxyphenyl O-pentylbenzoyl-laminaripentaoside
Sulfated butoxyphenyl O-octylbenzoyl-laminaripentaoside
Sulfated butoxyphenyl O-dodecylbenzoyl-laminaripentaoside
Sulfated butoxyphenyl O-acetyl-laminaripentaoside
Sulfated butoxyphenyl O-propionyl-laminaripentaoside
Sulfated butoxyphenyl O-butyryl-laminaripentaoside
Sulfated butoxyphenyl O-pentanoyl-laminaripentaoside
Sulfated butoxyphenyl O-hexanoyl-laminaripentaoside
Sulfated butoxyphenyl O-octanoyl-laminaripentaoside
Sulfated butoxyphenyl O-hexadecanoyl-laminaripentaoside
Sulfated butoxyphenyl O-docosanoyl-laminaripentaoside
Sulfated octyloxyphenyl O-benzoyl-laminaripentaoside
Sulfated octyloxyphenyl O-p-fluorobenzoyl-laminaripentaoside
Sulfated octyloxyphenyl O-2,4-di-fluorobenzoyl-laminaripentaoside
Sulfated octyloxyphenyl O-methylbenzoyl-laminaripentaoside
Sulfated octyloxyphenyl O-pentylbenzoyl-laminaripentaoside
Sulfated octyloxyphenyl O-octylbenzoyl-laminaripentaoside
Sulfated octyloxyphenyl O-dodecylbenzoyl-laminaripentaoside
Sulfated octyloxyphenyl O-acetyl-laminaripentaoside
Sulfated octyloxyphenyl O-propionyl-laminaripentaoside
Sulfated octyloxyphenyl O-butyryl-laminaripentaoside
Sulfated octyloxyphenyl O-pentanoyl-laminaripentaoside
Sulfated octyloxyphenyl O-hexanoyl-laminaripentaoside
Sulfated octyloxyphenyl O-octanoyl-laminaripentaoside
Sulfated octyloxyphenyl O-hexadecanoyl-laminaripentaoside
Sulfated octyloxyphenyl O-docosanoyl-laminaripentaoside
Sulfated n-dodecyl O-benzoyl-maltopentaoside
Sulfated n-dodecyl O-p-fluorobenzoyl-maltopentaoside
Sulfated n-dodecyl O-2,4-di-fluorobenzoyl-maltopentaoside
Sulfated n-dodecyl O-methylbenzoyl-maltopentaoside
Sulfated n-dodecyl O-pentylbenzoyl-maltopentaoside
Sulfated n-dodecyl O-octylbenzoyl-maltopentaoside
Sulfated n-dodecyl O-dodecylbenzoyl-maltopentaoside
Sulfated butylphenyl O-benzoyl-maltopentaoside
Sulfated butylphenyl O-p-fluorobenzoyl-maltopentaoside
Sulfated butylphenyl O-2,4-di-fluorobenzoyl-maltopentaoside
Sulfated butylphenyl O-methylbenzoyl-maltopentaoside
Sulfated butylphenyl O-pentylbenzoyl-maltopentaoside
Sulfated butylphenyl O-octylbenzoyl-maltopentaoside
Sulfated butylphenyl O-dodecylbenzoyl-maltopentaoside
Sulfated butylphenyl O-acetyl-maltopentaoside
Sulfated butylphenyl O-propionyl-maltopentaoside
Sulfated butylphenyl O-butyryl-maltopentaoside
Sulfated butylphenyl O-pentanoyl-maltopentaoside
Sulfated butylphenyl O-hexanoyl-maltopentaoside
Sulfated butylphenyl O-octanoyl-maltopentaoside
Sulfated butylphenyl O-hexadecanoyl-maltopentaoside
Sulfated butylphenyl O-docosanoyl-maltopentaoside
Sulfated heptylphenyl O-benzoyl-maltopentaoside
Sulfated heptylphenyl O-p-fluorobenzoyl-maltopentaoside
Sulfated heptylphenyl O-2,4-di-fluorobenzoyl-maltopentaoside
Sulfated heptylphenyl O-methylbenzoyl-maltopentaoside
Sulfated heptylphenyl O-pentylbenzoyl-maltopentaoside
Sulfated heptylphenyl O-octylbenzoyl-maltopentaoside
Sulfated heptylphenyl O-dodecylbenzoyl-maltopentaoside
Sulfated heptylphenyl O-acetyl-maltopentaoside
Sulfated heptylphenyl O-propionyl-maltopentaoside
Sulfated heptylphenyl O-butyryl-maltopentaoside
Sulfated heptylphenyl O-pentanoyl-maltopentaoside
Sulfated heptylphenyl O-hexanoyl-maltopentaoside
Sulfated heptylphenyl O-octanoyl-maltopentaoside Sulfated heptylphenyl O-hexadecanoyl-maltopentaoside
Sulfated heptylphenyl O-docosanoyl-maltopentaoside
Sulfated octylphenyl O-benzoyl-maltopentaoside
Sulfated octylphenyl O-p-fluorobenzoyl-maltopentaoside
Sulfated octylphenyl O-2,4-di-fluorobenzoyl-maltopentaoside
Sulfated octylphenyl O-methylbenzoyl-maltopentaoside
Sulfated octylphenyl O-pentylbenzoyl-maltopentaoside
Sulfated octylphenyl O-octylbenzoyl-maltopentaoside
Sulfated octylphenyl O-dodecylbenzoyl-maltopentaoside
Sulfated octylphenyl O-acetyl-maltopentaoside
Sulfated octylphenyl O-propionyl-maltopentaoside
Sulfated octylphenyl O-butyryl-maltopentaoside
Sulfated octylphenyl O-pentanoyl-maltopentaoside
Sulfated octylphenyl O-hexanoyl-maltopentaoside
Sulfated octylphenyl O-octanoyl-maltopentaoside
Sulfated octylphenyl O-hexadecanoyl-maltopentaoside
Sulfated octylphenyl O-docosanoyl-maltopentaoside
Sulfated methoxyphenyl O-benzoyl-maltopentaoside
Sulfated methoxyphenyl O-p-fluorobenzoyl-maltopentaoside
Sulfated methoxyphenyl O-2,4-di-fluorobenzoyl-maltopentaoside
Sulfated methoxyphenyl O-methylbenzoyl-maltopentaoside
Sulfated methoxyphenyl O-pentylbenzoyl-maltopentaoside
Sulfated methoxyphenyl O-octylbenzoyl-maltopentaoside
Sulfated methoxyphenyl O-dodecylbenzoyl-maltopentaoside
Sulfated methoxyphenyl O-acetyl-maltopentaoside
Sulfated methoxyphenyl O-propionyl-maltopentaoside
Sulfated methoxyphenyl O-butyryl-maltopentaoside
Sulfated methoxyphenyl O-pentanoyl-maltopentaoside
Sulfated methoxyphenyl O-hexanoyl-maltopentaoside
Sulfated methoxyphenyl O-octanoyl-maltopentaoside
Sulfated methoxyphenyl O-hexadecanoyl-maltopentaoside
Sulfated methoxyphenyl O-docosanoyl-maltopentaoside
Sulfated butoxyphenyl O-benzoyl-maltopentaoside
Sulfated butoxyphenyl O-p-fluorobenzoyl-maltopentaoside
Sulfated butoxyphenyl O-2,4-di-fluorobenzoyl-maltopentaoside
Sulfated butoxyphenyl O-methylbenzoyl-maltopentaoside
Sulfated butoxyphenyl O-pentylbenzoyl-maltopentaoside
Sulfated butoxyphenyl O-octylbenzoyl-maltopentaoside
Sulfated butoxyphenyl O-dodecylbenzoyl-maltopentaoside
Sulfated butoxyphenyl O-acetyl-maltopentaoside
Sulfated butoxyphenyl O-propionyl-maltopentaoside
Sulfated butoxyphenyl O-butyryl-maltopentaoside
Sulfated butoxyphenyl O-pentanoyl-maltopentaoside
Sulfated butoxyphenyl O-hexanoyl-maltopentaoside
Sulfated butoxyphenyl O-octanoyl-maltopentaoside
Sulfated butoxyphenyl O-hexadecanoyl-maltopentaoside
Sulfated butoxyphenyl O-docosanoyl-maltopentaoside
Sulfated octyloxyphenyl O-benzoyl-maltopentaoside
Sulfated octyloxyphenyl O-p-fluorobenzoyl-maltopentaoside
Sulfated octyloxyphenyl O-2,4-di-fluorobenzoyl-maltopentaoside
Sulfated octyloxyphenyl O-methylbenzoyl-maltopentaoside
Sulfated octyloxyphenyl O-pentylbenzoyl-maltopentaoside
Sulfated octyloxyphenyl O-octylbenzoyl-maltopentaoside
Sulfated octyloxyphenyl O-dodecylbenzoyl-maltopentaoside
Sulfated octyloxyphenyl O-acetyl-maltopentaoside
Sulfated octyloxyphenyl O-propionyl-maltopentaoside
Sulfated octyloxyphenyl O-butyryl-maltopentaoside
Sulfated octyloxyphenyl O-pentanoyl-maltopentaoside
Sulfated octyloxyphenyl O-hexanoyl-maltopentaoside
Sulfated octyloxyphenyl O-octanoyl-maltopentaoside
Sulfated octyloxyphenyl O-hexadecanoyl-maltopentaoside
Sulfated octyloxyphenyl O-docosanoyl-maltopentaoside
Sulfated n-dodecyl O-benzoyl-isomaltopentaoside
Sulfated n-dodecyl O-p-fluorobenzoyl-isomaltopentaoside
Sulfated n-dodecyl O-2,4-di-fluorobenzoyl-isomaltopentaoside
Sulfated n-dodecyl O-methylbenzoyl-isomaltopentaoside
Sulfated n-dodecyl O-pentylbenzoyl-isomaltopentaoside
Sulfated n-dodecyl O-octylbenzoyl-isomaltopentaoside
Sulfated n-dodecyl O-dodecylbenzoyl-isomaltopentaoside
Sulfated butylphenyl O-benzoyl-isomaltopentaoside
Sulfated butylphenyl O-p-fluorobenzoyl-isomaltopentaoside
Sulfated butylphenyl O-2,4-di-fluorobenzoyl-isomaltopentaoside
Sulfated butylphenyl O-methylbenzoyl-isomaltopentaoside
Sulfated butylphenyl O-pentylbenzoyl-isomaltopentaoside
Sulfated butylphenyl O-octylbenzoyl-isomaltopentaoside
Sulfated butylphenyl O-dodecylbenzoyl-isomaltopentaoside
Sulfated butylphenyl O-acetyl-isomaltopentaoside
Sulfated butylphenyl O-propionyl-isomaltopentaoside
Sulfated butylphenyl O-butyryl-isomaltopentaoside
Sulfated butylphenyl O-pentanoyl-isomaltopentaoside
Sulfated butylphenyl O-hexanoyl-isomaltopentaoside
Sulfated butylphenyl O-octanoyl-isomaltopentaoside
Sulfated butylphenyl O-hexadecanoyl-isomaltopentaoside
Sulfated butylphenyl O-docosanoyl-isomaltopentaoside
Sulfated heptylphenyl O-benzoyl-isomaltopentaoside
Sulfated heptylphenyl O-p-fluorobenzoyl-isomaltopentaoside
Sulfated heptylphenyl O-2,4-di-fluorobenzoyl-isomaltopentaoside
Sulfated heptylphenyl O-methylbenzoyl-isomaltopentaoside Sulfated heptylphenyl O-pentylbenzoyl-isomaltopentaoside
Sulfated heptylphenyl O-octylbenzoyl-isomaltopentaoside
Sulfated heptylphenyl O-dodecylbenzoyl-isomaltopentaoside
Sulfated heptylphenyl O-acetyl-isomaltopentaoside
Sulfated heptylphenyl O-propionyl-isomaltopentaoside
Sulfated heptylphenyl O-butyryl-isomaltopentaoside
Sulfated heptylphenyl O-pentanoyl-isomaltopentaoside
Sulfated heptylphenyl O-hexanoyl-isomaltopentaoside
Sulfated heptylphenyl O-octanoyl-isomaltopentaoside
Sulfated heptylphenyl O-hexadecanoyl-isomaltopentaoside
Sulfated heptylphenyl O-docosanoyl-isomaltopentaoside
Sulfated octylphenyl O-benzoyl-isomaltopentaoside
Sulfated octylphenyl O-p-fluorobenzoyl-isomaltopentaoside
Sulfated octylphenyl O-2,4-di-fluorobenzoyl-isomaltopentaoside
Sulfated octylphenyl O-methylbenzoyl-isomaltopentaoside
Sulfated octylphenyl O-pentylbenzoyl-isomaltopentaoside
Sulfated octylphenyl O-octylbenzoyl-isomaltopentaoside
Sulfated octylphenyl O-dodecylbenzoyl-isomaltopentaoside
Sulfated octylphenyl O-acetyl-isomaltopentaoside
Sulfated octylphenyl O-propionyl-isomaltopentaoside
Sulfated octylphenyl O-butyryl-isomaltopentaoside
Sulfated octylphenyl O-pentanoyl-isomaltopentaoside
Sulfated octylphenyl O-hexanoyl-isomaltopentaoside
Sulfated octylphenyl O-octanoyl-isomaltopentaoside
Sulfated octylphenyl O-hexadecanoyl-isomaltopentaoside
Sulfated octylphenyl O-docosanoyl-isomaltopentaoside
Sulfated methoxyphenyl O-benzoyl-isomaltopentaoside
Sulfated methoxyphenyl O-p-fluorobenzoyl-isomaltopentaoside
Sulfated methoxyphenyl O-2,4-di-fluorobenzoyl-isomaltopentaoside Sulfated methoxyphenyl O-methylbenzoyl-isomaltopentaoside
Sulfated methoxyphenyl O-pentylbenzoyl-isomaltopentaoside
Sulfated methoxyphenyl O-octylbenzoyl-isomaltopentaoside
Sulfated methoxyphenyl O-dodecylbenzoyl-isomaltopentaoside
Sulfated methoxyphenyl O-acetyl-isomaltopentaoside
Sulfated methoxyphenyl O-propionyl-isomaltopentaoside
Sulfated methoxyphenyl O-butyryl-isomaltopentaoside
Sulfated methoxyphenyl O-pentanoyl-isomaltopentaoside
Sulfated methoxyphenyl O-hexanoyl-isomaltopentaoside
Sulfated methoxyphenyl O-octanoyl-isomaltopentaoside
Sulfated methoxyphenyl O-hexadecanoyl-isomaltopentaoside
Sulfated methoxyphenyl O-docosanoyl-isomaltopentaoside
Sulfated butoxyphenyl O-benzoyl-isomaltopentaoside
Sulfated butoxyphenyl O-p-fluorobenzoyl-isomaltopentaoside
Sulfated butoxyphenyl O-2,4-di-fluorobenzoyl-isomaltopentaoside
Sulfated butoxyphenyl O-methylbenzoyl-isomaltopentaoside
Sulfated butoxyphenyl O-pentylbenzoyl-isomaltopentaoside
Sulfated butoxyphenyl O-octylbenzoyl-isomaltopentaoside
Sulfated butoxyphenyl O-dodecylbenzoyl-isomaltopentaoside
Sulfated butoxyphenyl O-acetyl-isomaltopentaoside
Sulfated butoxyphenyl O-propionyl-isomaltopentaoside
Sulfated butoxyphenyl O-butyryl-isomaltopentaoside
Sulfated butoxyphenyl O-pentanoyl-isomaltopentaoside
Sulfated butoxyphenyl O-hexanoyl-isomaltopentaoside
Sulfated butoxyphenyl O-octanoyl-isomaltopentaoside
Sulfated butoxyphenyl O-hexadecanoyl-isomaltopentaoside
Sulfated butoxyphenyl O-docosanoyl-isomaltopentaoside
Sulfated octyloxyphenyl O-benzoyl-isomaltopentaoside
Sulfated octyloxyphenyl O-p-fluorobenzoyl-isomaltopentaoside
Sulfated octyloxyphenyl O-2,4-di-fluorobenzoyl-isomaltopentaoside
Sulfated octyloxyphenyl O-methylbenzoyl-isomaltopentaoside
Sulfated octyloxyphenyl O-pentylbenzoyl-isomaltopentaoside
Sulfated octyloxyphenyl O-octylbenzoyl-isomaltopentaoside
Sulfated octyloxyphenyl O-dodecylbenzoyl-isomaltopentaoside
Sulfated octyloxyphenyl O-acetyl-isomaltopentaoside
Sulfated octyloxyphenyl O-propionyl-isomaltopentaoside
Sulfated octyloxyphenyl O-butyryl-isomaltopentaoside
Sulfated octyloxyphenyl O-pentanoyl-isomaltopentaoside
Sulfated octyloxyphenyl O-hexanoyl-isomaltopentaoside
Sulfated octyloxyphenyl O-octanoyl-isomaltopentaoside
Sulfated octyloxyphenyl O-hexadecanoyl-isomaltopentaoside
Sulfated octyloxyphenyl O-docosanoyl-isomaltopentaoside
Sulfated n-dodecyl O-benzoyl-β-D-galactopyranosyl(1→4)-β-D-galactopyranosyl(1→4)-β-D-glucopyranoside
Sulfated n-dodecyl O-p-fluorobenzoyl-β-D-galactopyranosyl(1→4)-β-D-galactopyranosyl(1→4)-β-D-glucopyranoside
Sulfated n-dodecyl O-2,4-di-fluorobenzoyl-β-D-galactopyranosyl(1→4)-β-D-galactopyranosyl(1→4 )-β-D-glucopyranoside
Sulfated n-dodecyl O-methylbenzoyl-β-D-galactopyranosyl(1→4)-β-D-galactopyranosyl(1→4)-β-D-glucopyranoside
Sulfated n-dodecyl O-pentylbenzoyl-β-D-galactopyranosyl(1→4)-β-D-galactopyranosyl(1→4)-β-D-glucopyranoside
Sulfated n-dodecyl O-octylbenzoyl-β-D-galactopyranosyl(1→4)-β-D-galactopyranosyl(1→4)-β-D-glucopyranoside
Sulfated n-dodecyl O-dodecylbenzoyl-β-D-galactopyranosyl(1→4)-β-D-galactopyranosyl(1→4)-β-D-glucopyranoside
Sulfated butylphenyl O-benzoyl-β-D-galactopyranosyl(1→4)-β-D-galactopyranosyl(1→4)-β-D-glucopyranoside
Sulfated butylphenyl O-p-fluorobenzoyl-β-D-galactopyranosyl(1→4)-β-D-galactopyranosyl(1→4)-β-D-glucopyranoside
Sulfated butylphenyl O-2,4-di-fluorobenzoyl-β-D-galactopyranosyl(1→4)-β-D-galactopyranosyl(1→4 )-β-D-glucopyranoside
Sulfated butylphenyl O-methylbenzoyl-β-D-galactopyranosyl(1→4)-β-D-galactopyranosyl(1→4)-β-D-glucopyranoside
Sulfated butylphenyl O-pentylbenzoyl-β-D-galactopyranosyl(1→4)-β-D-galactopyranosyl(1→4)-β-D-glucopyranoside
Sulfated butylphenyl O-octylbenzoyl-β-D-galactopyranosyl(1→4)-β-D-galactopyranosyl(1→4)-β-D-glucopyranoside
Sulfated butylphenyl O-dodecylbenzoyl-β-D-galactopyranosyl(1→4)-β-D-galactopyranosyl(1→4)-β-D-glucopyranoside
Sulfated butylphenyl O-acetyl-β-D-galactopyranosyl(1→4)-β-D-galactopyranosyl(1→4)-β-D-glucopyranoside
Sulfated butylphenyl O-propionyl-β-D-galactopyranosyl(1→4)-β-D-galactopyranosyl(1→4)-β-D-glucopyranoside
Sulfated butylphenyl O-butyryl-β-D-galactopyranosyl(1→4)-β-D-galactopyranosyl(1→4)-β-D-glucopyranoside
Sulfated butylphenyl O-pentanoyl-β-D-galactopyranosyl(1→4)-β-D-galactopyranosyl(1→4)-β-D-glucopyranoside
Sulfated butylphenyl O-hexanoyl-β-D-galactopyranosyl(1→4)-β-D-galactopyranosyl(1→4)-β-D-glucopyranoside
Sulfated butylphenyl O-octanoyl-β-D-galactopyranosyl(1→4)-β-D-galactopyranosyl(1→4)-β-D-glucopyranoside
Sulfated butylphenyl O-hexadecanoyl-β-D-galactopyranosyl(1→4)-β-D-galactopyranosyl(1→4)-β-D-glucopyranoside
Sulfated butylphenyl O-docosanoyl-β-D-galactopyranosyl(1→4)-β-D-galactopyranosyl(1→4)-β-D-glucopyranoside
Sulfated heptylphenyl O-benzoyl-β-D-galactopyranosyl(1→4)-β-D-galactopyranosyl(1→4)-β-D-glucopyranoside
Sulfated heptylphenyl O-P-fluorobenzoyl-β-D-galactopyranosyl(1→4)-β-D-galactopyranosyl(1→4)-β-D-glucopyranoside
Sulfated heptylphenyl O-2,4-di-fluorobenzoyl-β-D-galactopyranosyl(1→4)-β-D-galactopyranosyl(1→4 )-β-D-glucopyranoside
Sulfated heptylphenyl O-methylbenzoyl-β-D-galactopyranosyl(1→4)-β-D-galactopyranosyl(1→4)-β-D-glucopyranoside
Sulfated heptylphenyl O-pentylbenzoyl-β-D-galactopyranosyl(1→4)-β-D-galactopyranosyl(1→4)-β-D-glucopyranoside Sulfated heptylphenyl O-octylbenzoyl-β-D-galactopyranosyl(1→4)-β-D-galactopyranosyl(1→4)-β-D-glucopyranoside Sulfated heptylphenyl O-dodecylbenzoyl-β-D-galactopyranosyl(1→4)-β-D-galactopyranosyl(1→4)-β-D-glucopyranoside Sulfated heptylphenyl O-acetyl-β-D-galactopyranosyl(1→4)-β-D-galactopyranosyl(1→4)-β-D-glucopyranoside Sulfated heptylphenyl O-propionyl-β-D-galactopyranosyl(1→4)-β-D-galactopyranosyl(1→4)-β-D-glucopyranoside Sulfated heptylphenyl O-butyryl-β-D-galactopyranosyl(1→4)-β-D-galactopyranosyl(1→4)-β-D-glucopyranoside Sulfated heptylphenyl O-pentanoyl-β-D-galactopyranosyl(1→4)-β-D-galactopyranosyl(1→4)-β-D-glucopyranoside Sulfated heptylphenyl O-hexanoyl-β-D-galactopyranosyl(1→4)-β-D-galactopyranosyl(1→4)-β-D-glucopyranoside Sulfated heptylphenyl O-octanoyl-β-D-galactopyranosyl(1→4)-β-D-galactopyranosyl(1→4)-β-D-glucopyranoside Sulfated heptylphenyl O-hexadecanoyl-β-D-galactopyranosyl(1→4) -β-D-galactopyranosyl(1→4)-β-D-glucopyranoside Sulfated heptylphenyl O-docosanoyl-β-D-galactopyranosyl(1→4)-β-D-galactopyranosyl(1→4)-β-D-glucopyranoside Sulfated octylphenyl O-benzoyl-β-D-galactopyranosyl(1→4)-β-D-galactopyranosyl(1→4)-β-D-glucopyranoside Sulfated octylphenyl O-p-fluorobenzoyl-β-D-galactopyranosyl(1→4)-β-D-galactopyranosyl(1→4)-β-D-glucopyranoside Sulfated octylphenyl O-2,4-di-fluorobenzoyl-β-D-galactopyranosyl(1→4)-β-D-galactopyranosyl(1→4 )-β-D-glucopyranoside Sulfated octylphenyl O-methylbenzoyl-β-D-galactopyranosyl(1→4)-β-D-galactopyranosyl(1→4)-β-D-glucopyranoside Sulfated octylphenyl O-pentylbenzoyl-β-D-galactopyranosyl(1→4)-β-D-galactopyranosyl(1→4)-β-D-glucopyranoside Sulfated octylphenyl O-octylbenzoyl-β-D-galactopyranosyl(1→4)-β-D-galactopyranosyl(1→4)-β-D-glucopyranoside Sulfated octylphenyl O-dodecylbenzoyl-β-D-galactopyranosyl(1→4)-β-D-galactopyranosyl(1→4)-β-D-glucopyranoside Sulfated octylphenyl O-acetyl-β-D-galactopyranosyl(1→4)-β-D-galactopyranosyl(1→4) -β-D-glucopyranoside Sulfated octylphenyl O-propionyl-β-D-galactopyranosyl(1→4)-β-D-galactopyranosyl(1→4)-β-D-glucopyranoside Sulfated octylphenyl O-butyryl-β-D-galactopyranosyl(1→4)-β-D-galactopyranosyl(1→4)-β-D-glucopyranoside Sulfated octylphenyl O-pentanoyl-β-D-galactopyranosyl(1→4)-β-D-galactopyranosyl(1→4)-β-D-glucopyranoside Sulfated octylphenyl O-hexanoyl-β-D-galactopyranosyl(1→4)-β-D-galactopyranosyl(1→4)-β-D-glucopyranoside Sulfated octylphenyl O-octanoyl-β-D-galactopyranosyl(1→4)-β-D-galactopyranosyl(1→4)-β-D-glucopyranoside Sulfated octylphenyl O-hexadecanoyl-β-D-galactopyranosyl(1→4)-β-D-galactopyranosyl(1→4)-β-D-glucopyranoside Sulfated octylphenyl O-docosanoyl-β-D-galactopyranosyl(1→4)-β-D-galactopyranosyl(1→4)-β-D-glucopyranoside Sulfated methoxyphenyl O-benzoyl-β-D-galactopyranosyl(1→4)-β-D-galactopyranosyl(1→4)-β-D-glucopyranoside Sulfated methoxyphenyl O-p-fluorobenzoyl-β-D-galactopyranosyl(1→4)-β-D-galactopyranosyl(1→4)-β-D-glucopyranoside Sulfated methoxyphenyl O-2,4-di-fluorobenzoyl-β-D-galactopyranosyl(1→4)-β-D-galactopyranosyl(1→4 )-β-D-glucopyranoside Sulfated methoxyphenyl O-methylbenzoyl-β-D-galactopyranosyl(1→4)-β-D-galactopyranosyl(1→4)-β-D-glucopyranoside Sulfated methoxyphenyl O-pentylbenzoyl-β-D-galactopyranosyl(1→4)-β-D-galactopyranosyl(1→4)-β-D-glucopyranoside Sulfated methoxyphenyl O-octylbenzoyl-β-D-galactopyranosyl(1→4)-β-D-galactopyranosyl(1→4)-β-D-glucopyranoside Sulfated methoxyphenyl O-dodecylbenzoyl-β-D-galactopyranosyl(1→4)-β-D-galactopyranosyl(1→4)-β-D-glucopyranoside Sulfated methoxyphenyl O-acetyl-β-D-galactopyranosyl(1→4)-β-D-galactopyranosyl(1→4)-β-D-glucopyranoside Sulfated methoxyphenyl O-propionyl-β-D-galactopyranosyl(1→4)-β-D-galactopyranosyl(1→4)-β-D-glucopyranoside Sulfated methoxyphenyl O-butyryl-β-D-galactopyranosyl(1→4)-β-D-galactopyranosyl(1→4)-β-D-glucopyranoside Sulfated methoxyphenyl O-pentanoyl-β-D-galactopyranosyl(1→4)-β-D-galactopyranosyl(1→4)-β-D-glucopyranoside Sulfated methoxyphenyl O-hexanoyl-β-D-galactopyranosyl(1→4)-β-D-galactopyranosyl(1→4)-β-D-glucopyranoside Sulfated methoxyphenyl O-octanoyl-β-D-galactopyranosyl(1→4)-β-D-galactopyranosyl(1→4)-β-D-glucopyranoside Sulfated methoxyphenyl O-hexadecanoyl-β-D-galactopyranosyl(1→4)-β-D-galactopyranosyl(1→4)-β-D-glucopyranoside Sulfated methoxyphenyl O-docosanoyl-β-D-galactopyranosyl(1→4)-β-D-galactopyranosyl(1→4)-β-D-glucopyranoside Sulfated butoxyphenyl O-benzoyl-β-D-galactopyranosyl(1→4)-β-D-galactopyranosyl(1→4)-β-D-glucopyranoside Sulfated butoxyphenyl O-p-fluorobenzoyl-β-D-galactopyranosyl(1→4)-β-D-galactopyranosyl(1→4)-β-D-glucopyranoside Sulfated butoxyphenyl O-2,4-di-fluorobenzoyl-β-D-galactopyranosyl(1→4)-β-D-galactopyranosyl(1→4 )-β-D-glucopyranoside Sulfated butoxyphenyl O-methylbenzoyl-β-D-galactopyranosyl(1→4)-β-D-galactopyranosyl(1→4)-β-D-glucopyranoside Sulfated butoxyphenyl O-pentylbenzoyl-β-D-galactopyranosyl(1→4)-β-D-galactopyranosyl(1→4)-β-D-glucopyranoside Sulfated butoxyphenyl O-octylbenzoyl-β-D-galactopyranosyl(1→4)-β-D-galactopyranosyl(1→4)-β-D-glucopyranoside Sulfated butoxyphenyl O-dodecylbenzoyl-β-D-galactopyranosyl(1→4)-β-D-galactopyranosyl(1→4)-β-D-glucopyranoside Sulfated butoxyphenyl O-acetyl-β-D-galactopyranosyl(1→4)-β-D-galactopyranosyl(1→4)-β-D-glucopyranoside Sulfated butoxyphenyl O-propionyl-β-D-galactopyranosyl(1→4)-β-D-galactopyranosyl(1→4)-β-D-glucopyranoside
Sulfated butoxyphenyl O-butyryl-β-D-galactopyranosyl(1→4)-β-D-galactopyranosyl(1→4)-β-D-glucopyranoside
Sulfated butoxyphenyl O-pentanoyl-β-D-galactopyranosyl(1→4)-β-D-galactopyranosyl(1→4)-β-D-glucopyranoside
Sulfated butoxyphenyl O-hexanoyl-β-D-galactopyranosyl(1→4)-β-D-galactopyranosyl(1→4)-β-D-glucopyranoside
Sulfated butoxyphenyl O-octanoyl-β-D-galactopyranosyl(1→4)-β-D-galactopyranosyl(1→4)-β-D-glucopyranoside
Sulfated butoxyphenyl O-hexadecanoyl-β-D-galactopyranosyl(1→4)-β-D-galactopyranosyl(1→4)-β-D-glucopyranoside
Sulfated butoxyphenyl O-docosanoyl-β-D-galactopyranosyl(1→4)-β-D-galactopyranosyl(1→4)-β-D-glucopyranoside
Sulfated octyloxyphenyl O-benzoyl-β-D-galactopyranosyl(1→4)-β-D-galactopyranosyl(1→4)-β-D-glucopyranoside
Sulfated octyloxyphenyl O-p-fluorobenzoyl-β-D-galactopyranosyl(1→4)-β-D-galactopyranosyl(1→4 )-β-D-glucopyranoside
Sulfated octyloxyphenyl O-2,4-di-fluorobenzoyl-β-D-galactopyranosyl(1→4)-β-D-galactopyranosyl(1→4 )-β-D-glucopyranoside
Sulfated octyloxyphenyl O-methylbenzoyl-β-D-galactopyranosyl(1→4)-β-D-galactopyranosyl(1→4)-β-D-glucopyranoside
Sulfated octyloxyphenyl O-pentylbenzoyl-β-D-galactopyranosyl(1→4)-β-D-galactopyranosyl(1→4)-β-D-glucopyranoside
Sulfated octyloxyphenyl O-octylbenzoyl-β-D-galactopyranosyl(1→4)-β-D-galactopyranosyl(1→4)-β-D-glucopyranoside
Sulfated octyloxyphenyl O-dodecylbenzoyl-β-D-galactopyranosyl(1→4)-β-D-galactopyranosyl(1→4)-β-D-glucopyranoside
Sulfated octyloxyphenyl O-acetyl-β-D-galactopyranosyl(1→4)-β-D-galactopyranosyl(1→4)-β-D-glucopyranoside
Sulfated octyloxyphenyl O-propionyl-β-D-galactopyranosyl(1→4)-β-D-galactopyranosyl(1→4)-β-D-glucopyranoside
Sulfated octyloxyphenyl O-butyryl-β-D-galactopyranosyl(1→4)-β-D-galactopyranosyl(1→4)-β-D-glucopyranoside
Sulfated octyloxyphenyl O-pentanoyl-β-D-galactopyranosyl(1→4)-β-D-galactopyranosyl(1→4)-β-D-glucopyranoside
Sulfated octyloxyphenyl O-hexanoyl-β-D-galactopyranosyl(1→4)-β-D-galactopyranosyl(1→4)-β-D-glucopyranoside
Sulfated octyloxyphenyl O-octanoyl-β-D-galactopyranosyl(1→4)-β-D-galactopyranosyl(1→4)-β-D-glucopyranoside
Sulfated octyloxyphenyl O-hexadecanoyl-β-D-galactopyranosyl(1→4)-β-D-galactopyranosyl(1→4)-β-D-glucopyranoside
Sulfated octyloxyphenyl O-docosanoyl-β-D-galactopyranosyl(1→4)-β-D-galactopyranosyl(1→4)-β-D-glucopyranoside
Sulfated dl-α-tocopheryl O-benzoyl-laminaripentaoside
Sulfated dl-α-tocopheryl O-p-fluorobenzoyl-laminaripentaoside
Sulfated dl-α-tocopheryl O-2,4-di-fluorobenzoyl-laminaripentaoside
Sulfated dl-α-tocopheryl O-methylbenzoyl-laminaripentaoside
Sulfated dl-α-tocopheryl O-pentylbenzoyl-laminaripentaoside
Sulfated dl-α-tocopheryl O-octylbenzoyl-laminaripentaoside
Sulfated dl-α-tocopheryl O-dodecylbenzoyl-laminaripentaoside
Sulfated dl-α-tocopheryl O-acetyl-laminaripentaoside
Sulfated dl-α-tocopheryl O-propionyl-laminaripentaoside
Sulfated dl-α-tocopheryl O-butyryl-laminaripentaoside
Sulfated dl-α-tocopheryl O-pentanoyl-laminaripentaoside
Sulfated dl-α-tocopheryl O-hexanoyl-laminaripentaoside
Sulfated dl-α-tocopheryl O-heptanoyl-laminaripentaoside
Sulfated dl-α-tocopheryl O-octanoyl-laminaripentaoside
Sulfated dl-α-tocopheryl O-dodecanoyl-laminaripentaoside
Sulfated dl-α-tocopheryl O-hexadecanoyl-laminaripentaoside
Sulfated dl-α-tocopheryl O-docosanoyl-laminaripentaoside
Sulfated dl-α-tocopheryl O-tricosanoyl-laminaripentaoside
Sulfated dl-α-tocopheryl O-benzoyl-maltopentaoside
Sulfated dl-α-tocopheryl O-p-fluorobenzoyl-maltopentaoside
Sulfated dl-α-tocopheryl O-2,4-di-fluorobenzoyl-maltopentaoside
Sulfated dl-α-tocopheryl O-methylbenzoyl-maltopentaoside
Sulfated dl-α-tocopheryl O-pentylbenzoyl-maltopentaoside
Sulfated dl-α-tocopheryl O-octylbenzoyl-maltopentaoside
Sulfated dl-α-tocopheryl O-dodecylbenzoyl-maltopentaoside
Sulfated dl-α-tocopheryl O-acetyl-maltopentaoside
Sulfated dl-α-tocopheryl O-propionyl-maltopentaoside
Sulfated dl-α-tocopheryl O-butyryl-maltopentaoside
Sulfated dl-α-tocopheryl O-pentanoyl-maltopentaoside
Sulfated dl-α-tocopheryl O-hexanoyl-maltopentaoside
Sulfated dl-α-tocopheryl O-heptanoyl-maltopentaoside
Sulfated dl-α-tocopheryl O-octanoyl-maltopentaoside
Sulfated dl-α-tocopheryl O-dodecanoyl-maltopentaoside
Sulfated dl-α-tocopheryl O-hexadecanoyl-maltopentaoside
Sulfated dl-α-tocopheryl O-docosanoyl-maltopentaoside
Sulfated dl-α-tocopheryl O-tricosanoyl-maltopentaoside
Sulfated dl-α-tocopheryl O-benzoyl-isomaltopentaoside
Sulfated dl-α-tocopheryl O-p-fluorobenzoyl-isomaltopentaoside
Sulfated dl-α-tocopheryl O-2,4-di-fluorobenzoyl-isomaltopentaoside
Sulfated dl-α-tocopheryl O-methylbenzoyl-isomaltopentaoside
Sulfated dl-α-tocopheryl O-pentylbenzoyl-isomaltopentaoside
Sulfated dl-α-tocopheryl O-octylbenzoyl-isomaltopentaoside
Sulfated dl-α-tocopheryl O-dodecylbenzoyl-isomaltopentaoside
Sulfated dl-α-tocopheryl O-acetyl-isomaltopentaoside
Sulfated dl-α-tocopheryl O-propionyl-isomaltopentaoside
Sulfated dl-α-tocopheryl O-butyryl-isomaltopentaoside
Sulfated dl-α-tocopheryl O-pentanoyl-isomaltopentaoside
Sulfated dl-α-tocopheryl O-hexanoyl-isomaltopentaoside
Sulfated dl-α-tocopheryl O-heptanoyl-isomaltopentaoside
Sulfated dl-α-tocopheryl O-octanoyl-isomaltopentaoside
Sulfated dl-α-tocopheryl O-dodecanoyl-isomaltopentaoside
Sulfated dl-α-tocopheryl O-hexadecanoyl-isomaltopentaoside Sulfated dl-α-tocopheryl O-docosanoyl-isomaltopentaoside
Sulfated dl-α-tocopheryl O-tricosanoyl-isomaltopentaoside
Sulfated dl-α-tocopheryl O-benzoyl-β-D-galactopyranosyl(1→4)-β-D-galactopyranosyl(1→4 )-β-D-glucopyranosidepentaoside
Sulfated dl-α-tocopheryl O-p-fluorobenzoyl-β-D-galactopyranosyl(1→4 )-β-D-galactopyranosyl(1→4)-β-D-glucopyranosidepentaoside
Sulfated dl-α-tocopheryl O-2,4-di-fluorobenzoyl-β-D-galactopyranosyl(1→4 )-β-D-galactopyranosyl(1→4)-β-D-glucopyranosidepentaoside
Sulfated dl-α-tocopheryl O-methylbenzoyl-β-D-galactopyranosyl(1→4 )-β-D-galactopyranosyl(1→4)-β-D-glucopyranosidepentaoside
Sulfated dl-α-tocopheryl O-pentylbenzoyl-β-D-galactopyranosyl(1→4 )-β-D-galactopyranosyl(1→4)-β-D-glucopyranosidepentaoside
Sulfated dl-α-tocopheryl O-octylbenzoyl-β-D-galactopyranosyl(1→4 )-β-D-galactopyranosyl(1→4)-β-D-glucopyranosidepentaoside
Sulfated dl-α-tocopheryl O-dodecylbenzoyl-β-D-galactopyranosyl(1→4 )-β-D-galactopyranosyl(1→4)-β-D-glucopyranosidepentaoside
Sulfated dl-α-tocopheryl O-acetyl-β-D-galactopyranosyl(1→4)-β-D-galactopyranosyl(1→4 )-β-D-glucopyranosidepentaoside
Sulfated dl-α-tocopheryl O-propionyl-β-D-galactopyranosyl(1→4 )-β-D-galactopyranosyl(1→4)-β-D-glucopyranosidepentaoside
Sulfated dl-α-tocopheryl O-butyryl-β-D-galactopyranosyl(1→4)-β-D-galactopyranosyl(1→4 )-β-D-glucopyranosidepentaoside
Sulfated dl-α-tocopheryl O-pentanoyl-β-D-galactopyranosyl-(1→4)-β-D-galactopyranosyl(1→4 )-β-D-glucopyranosidepentaoside
Sulfated dl-α-tocopheryl O-hexanoyl-β-D-galactopyranosyl(1→4)-β-D-galactopyranosyl(1→4 )-β-D-glucopyranosidepentaoside
Sulfated dl-α-tocopheryl O-heptanoyl-β-D-galactopyranosyl(1→4)-β-D-galactopyranosyl(1→4 )-β-D-glucopyranoside pentaoside
Sulfated dl-α-tocopheryl O-octanoyl-β-D-galactopyranosyl(1→4)-β-D-galactopyranosyl(1→4 )-β-D-glucopyranosidepentaoside
Sulfated dl-α-tocopheryl O-dodecanoyl-β-D-galactopyranosyl(1→4)-β-D-galactopyranosyl(1→4 )-β-D-glucopyranosidepentaoside
Sulfated dl-α-tocopheryl O-hexadecanoyl-β-D-galactopyranosyl(1→4)-β-D-galactopyranosyl(1→4 )-β-D-glucopyranosidepentaoside
Sulfated dl-α-tocopheryl O-docosanoyl-β-D-galactopyranosyl(1→4)-β-D-galactopyranosyl(1→4 )-β-D-glucopyranosidepentaoside
Sulfated dl-α-tocopheryl O-tricosanoyl-β-D-galactopyranosyl(1→4)-β-D-galactopyranosyl(1→4 )-β-D-glucopyranosidepentaoside The antiviral agent according to the present invention exhibits an antiviral activity on various viruses. Thus it is useful in the treatment of diseases induced by pathogenic viruses and conjugated infections caused by Retro viruses such as HIV. In particular, it shows an excellent antiviral activity on HIV.

Although the function mechanism of the antiviral agent according to the present invention has not been clarified in detail, it is estimated that it might inhibit the attachment of a virus to the target cells similar to the conventionally known sulfated polysaccharide. The compound of the present invention is characterized by having been converted into a glycoside and thus showing a significantly improved long-lasting antiviral action (compared with non-glycoside compounds) and having significantly improved oral absorption characteristics (compared with sulfated polysaccharides and sulfated oligoglycoside) due to the introduction of acyl groups.

The compound of the present invention is effective in suppressing diseases caused by viruses. In particular, it exhibits a remarkable antiviral action on HIV. Thus the compound of the present invention is useful as an antiviral agent. That is to say, it is useful in the suppression, prevention and treatment of diseases caused by these viruses. It can be administered by various ways including intravenous administration, oral administration, intramuscular administration, intraperitoneal administration and intrarectal administration.

The antiviral agent according to the present invention may be formulated into common preparations such as tablets, capsules, granules, pills, solutions, injections, syrups and suppositories and either orally or parenterally administered, though, needless to say, the preparation form varies depending on the administration route. These preparations preferably contains from 0.1 to 100% of the compound of the present invention as an active ingredient.

As a means therefor, fillers and additives commonly employed for the production of drugs can be used. Examples of the common fillers include water, physiological saline, alcohols, polyethylene glycol, glycerol esters, gelatin, carbohydrates, magnesium stearate and talc. Examples of the common additives include preservatives, sterilizers, lubricants, coatings, humectants, emulsifiers, coloring agents, masking flavors and perfumes.

The dose of the antiviral agent according to the present invention varies depending on the form and frequency of the administration, the conditions and body weight of the patient and the severity of the disease. In general, it is preferable to administer the antiviral agent in a dose of from 0.1 to 150 mg, still preferably from 0.5 to 100 mg, per kg of the body weight once to thrice a day. The administration frequency is also determined depending on the form of the drug, the conditions and body weight of the patient and the severity of the disease. It may be administered via intravenous drip infusion.

In addition, the compound of the present invention is a safe compound which has a low toxicity in vivo and causes no death of mice when administered in a dose of 1 g/kg. Further, the compound of the present invention has a lower anticoagulant activity than dextran sulfate which is one of sulfated polysaccharides. Furthermore, it shows a long-lasting antiviral action in the blood which is never observed in the case of the conventional sulfated polysaccharides. Based on these facts, it has been proved that the compound of the present invention is a highly effective one.

In an acute toxicity test wherein the antiviral agents of the present invention were orally administered to mice, the administration of each of the compounds given in the following Examples in a single dose of 1.0 g/kg caused no death. That is to say, each of the compounds of the present invention shows a 50% lethal dose ($LD_{50}$) exceeding 1 g/kg in the oral administration. When intravenously injected into mice, a typical example of the compound of the present invention showed an $LD_{50}$ exceeding 300 mg/kg. These results indicate that the antiviral agent of the present invention is a compound having an extremely low toxicity.

The present invention now will be illustrated in greater detail by way of the following examples, but it should be understood that the present invention is not to be contstrued as being limited thereby.

REFERENCE SYNTHESIS EXAMPLE 1

Synthesis of n-dodecyl β-D-laminaripentaoside

First, 0.55 g of sodium acetate and 10 ml of acetic anhydride were heated in a flask, to which 1.003 g of laminaripentaose was added little by little, and the mixture was heated under reflux for 2 hours. The reaction mixture was poured on 100 g of ice, and the reaction products were extracted with ethyl acetate. The ethyl acetate layer was dried with anhydrous sodium sulfate and then concentrated to produce syrup. The yield was over 90%. Its α/β ratio, as determined by nuclear magnetic resonance spectral analysis, was about 25/75.

Specific rotation: $[\alpha]_D = -43.5°$ (c=1.0/chloroform) (25° C.)

Next, 500 mg of the peracetyl laminaripentaose prepared above and 60 mg of n-dodecanol were dissolved in 20 ml of dichloromethane in a 50 ml three-necked flask, to which 1 mmol of tin tetrachloride was added and allowed to react at room temperature for 20 hours in an atmosphere of nitrogen. The reaction mixture was poured into sodium bicarbonate solution, filtered by a celite-coated funnel, extracted with dichloromethane, dried with anhydrous sodium sulfate, and concentrated. The residue was further refined by column chromatography (silica gel, hexane/ethyl acetate), and the main fraction of Rf=0.72 by t.l.c. was collected and concentrated. The obtained product was 0.265 g (yield: 49%). The product was n-dodecyl peracetyl-β-D-laminaripentaoside, as identified by the nuclear magnetic resonance spectral analysis.

Specific rotation: $[\alpha]_D = -42.8°$ (c=1.0/chloroform) (28° C.)

Next, 238 mg of the peracetate of glycoside prepared above, was dissolved in 10 ml of methanol, to which 4.3 ml of 0.1N sodium methoxidemethanol solution was added at room temperature. The mixture was stirred for 2.5 hours and treated with an ion-exchanging resin to remove sodium ions. The methanol solution was concentrated and solidified after the ion-exchanging resin was removed by filtration in order to prepare 138 mg of the target product.

Specific rotation: $[\alpha]_D = -16.4°$ (c=0.50/methanol) (30° C.)

COMPOUND EXAMPLE 1

Synthesis of Sulfated n-dodecyl O-benzoyl-β-D-laminaripentaoside (1): (Compound 1)

600 mg of n-dodecyl β-D-laminaripentaoside, prepared by the method similar to that used for REFERENCE SYNTHESIS EXAMPLE 1, was dissolved in 30 ml of dried pyridine under nitrogen atmosphere at about 0° C., to which 460 mg of benzoyl chloride was added with dropwise to keep 0°–3° C., and the mixture was stirred at the same temperature for 20 minutes and that stirred for 19.5 hours at room temperature. The mixture was then poured into 150 g of ice and water. This was extracted three times with 100 ml portions of ethyl acetate. The ethyl acetate solution was washed successively with water, dried with anhydrous sodium sulfate, and evaporated to yield 840 mg of the dodecyl-O-benzoyl-β-D-laminaripentaoside. Proton magnetic resonance (PMR) spectroscopy data (ppm) (CDCl$_3$, TMS) was as follows. 0.85(3H), 1.15–1.33(18H), 1.40–1.55(2H), 3.1–3.9 (32H), 4.1–5.7(hydroxy protons and anomeric protons), 7.45–7.55(11.2H), 7.6(5.6H), 7.9–8.1(11.2H)

From the data, the percent of acyl groups in molecule is 37%.

Next, to 406 mg of the benzoyl glycoside was added 10 ml of dried pyridine. The mixture was evaporated at reduced pressure and 10 ml of dried pyridine was added to the residue. The solution under an argon atmosphere, was heated to 85° C., and to the mixture was added 480 mg of sulfur trioxide pyridine complex. This mixture was stirred for 2 hours at the same temperature. It was then cooled to room temperature, from which oily precipitate was separated. To the precipitate was added 15 ml of water, which was adjusted to a pH level of 7.2 with barium hydroxide solution, and the solids were separated centrifugally therefrom. The solids were washed with water. The mixed solution of the supernatant and washed water was allowed to pass through a Na ion-exchanging column to produce sodium salts. The effluent was concentrated to 5 ml and poured into 200 ml of acetone, and the precipitates formed were collected by centrifugation. After the precipitates were dissolved into 20 ml of water and the solution was adjusted again to a pH 7.11 with 0.2N HCl solution, the adjusted solution was freezed and lyophilized to remove water to produce 440 mg of the target compound.

Specific rotation: $[\alpha]_D = -19.9°$ (c=0.4/H$_2$O) (30° C.)

Infrared absorption frequencies (I.R.) (cm$^{-1}$) 3430, 3050, 2930, 2850, 1720, 1630, 1450, 1240, 1120, 800, 720

Proton magnetic resonance (PMR) spectra (D$_2$O) (ppm) 0.84 alkyl methyl (3H) 1.1–1.8 alkyl methylene (18H) 1.45–1.55 (2H) 3.4–5.5 7.35–7.70 (16.8H) 7.85–8.1 (11.2H)

The percent of acyl groups in the compound to be calculated from the PMR data: 35%.

The percent of sulfate groups in the compound to be calculated from the elementary analysis value: 51%.

COMPOUND EXAMPLE 2

Synthesis of Sulfated n-dodecyl O-benzoyl-β-D-laminaripentaoside (2): (Compound 2)

By using 0.16 ml of benzoyl chloride, 760 mg of n-dodecyl O-benzoyl-β-D-laminaripentaoside was prepared from 600 mg of dodecyl β-D-laminaripentaoside. This benzoate was reacted with 1.0 g of sulfur trioxide pyridine complex, in a manner similar to that for COMPOUND EXAMPLE 1. The yield of the target compound was 760 mg.

Specific rotation: $[\alpha]_D = -14.4°$ (c=0.4/H$_2$O) (30° C.)

Infrared absorption frequencies (I.R.) (cm$^{-1}$) 3400, 2900, 2850, 1710, 1630, 1450, 1240, 980, 800, 720

PMR spectra (D$_2$O) (ppm) 0.86(3H) 1.1–1.3(18H) 1.5–1.6(2H) 3.4–5.3 7.40–7.70(6.9H) 7.85–8.1(4.6H)

The percent of acyl groups in the compound to be calculated from the PMR data: 14%.

The percent of sulfate groups in the compound to be calculated from the elementary analysis value: 66%.

COMPOUND EXAMPLE 3

Synthesis of Sulfated n-dodecyl O-4-fluorobenzoyl-β-D-laminaripentaoside (1): (Compound 3)

By using 280 mg of 4-fluorobenzoyl chloride, 720 mg of n-dodecyl O-4-fluorobenzoyl-β-D-laminaripentaoside was prepared from 600 mg of n-dodecyl β-D-laminaripentaoside. This fluorobenzoate was reacted with 0.54 g of sulfur trioxide pyridine complex, in a manner similar to that for COMPOUND EXAMPLE 1. The yield of the target compound was 430 mg.

Specific rotation: $[\alpha]_D=-9.2°$ (c=0.4/H$_2$O) (30° C.)

Infrared absorption frequencies (I.R.) (cm$^{-1}$) 3450, 2930, 2850, 1720, 1600, 1510, 1240, 1160, 800, 770

PMR spectra (D$_2$O) (ppm) 0.85(3H) 1.15–1.35(18H) 1.5–1.6(2H) 3.4–5.5 7.15–7.35(6H) 8.00–8.2(6H)

The percent of acyl groups in the compound to be calculated from the PMR data: 19%.

The percent of sulfate groups in the compound to be calculated from the elementary analysis value: 59%.

COMPOUND EXAMPLE 4

Synthesis of Sulfated n-dodecyl O-4-fluorobenzoyl-β-D-laminaripentaoside (2): (Compound 4)

By using 370 mg of 4-fluorobenzoyl chloride, 620 mg of n-dodecyl O-4-fluorobenzoyl-β-D-laminaripentaoside was prepared from 600 mg of n-dodecyl β-D-laminaripentaoside. The fluorobenzoate (400 mg) was reacted with 0.47 g of sulfur trioxide pyridine complex, in a manner similar to that for COMPOUND EXAMPLE 1. The yield of the target compound was 430 mg.

Specific rotation: $[\alpha]_D=-20.1°$ (c=0.4/H$_2$O) (30° C.)

Infrared absorption frequencies (I.R.) (cm$^{-1}$) 3400, 2930, 2850, 1720, 1630, 1600, 1410, 1240, 1160, 990, 800, 770

PMR spectra (D$_2$O) (ppm) 0.86(3H) 1.15–1.30(18H) 1.5–1.6(2H) 3.4–5.5 7.00–7.40(8.2H) 8.00–8.15(8.2H)

The percent of acyl groups in the compound to be calculated from the PMR data: 26%.

The percent of sulfate groups in the compound to be calculated from the elementary analysis value: 56%.

COMPOUND EXAMPLE 5

Synthesis of Sulfated n-dodecyl O-4-fluorobenzoyl-β-D-laminaripentaoside (3): (Compound 5)

By using 220 mg of 4-fluorobenzoyl chloride, 720 mg of n-dodecyl O-4-fluorobenzoyl-β-D-laminaripentaoside was prepared from 600 mg of n-dodecyl β-D-laminaripentaoside. The fluorobenzoate (400 mg) was reacted with 0.540 g of sulfur trioxide pyridine complex, in a manner similar to that for COMPOUND EXAMPLE 1. The yield of the target compound was 680 mg.

Specific rotation: $[\alpha]_D=-12.0°$ (c=0.4/H$_2$O) (30° C.)

Infrared absorption frequencies (I.R.) (cm$^{-1}$) 3400, 2900, 2850, 1700, 1630, 1510, 1220, 990, 800

PMR spectra (D$_2$O) (ppm) 0.86(3H) 1.15–1.30(18H) 1.5–1.6(2H) 3.4–5.5 7.10–7.35(4.8H) 8.00–8.20(4.8H)

The percent of acyl groups in the compound to be calculated from the PMR data: 15%.

The percent of sulfate groups in the compound to be calculated from the elementary analysis value: 63%.

COMPOUND EXAMPLE 6

Synthesis of Sulfated n-dodecyl O-2,4-difluorobenzoyl-β-D-laminaripentaoside (1): (Compound 6)

By using 330 mg of 2,4-difluorobenzoyl chloride, 830 mg of n-dodecyl O-2,4-difluorobenzoyl-β-D-laminaripentaoside was prepared from 600 mg of n-dodecyl β-D-laminaripentaoside. The difluorobenzoate (400 mg) was reacted with 550 mg of sulfur trioxide pyridine complex, in a manner similar to that for COMPOUND EXAMPLE 1. The yield of the target compound was 502 mg.

Specific rotation: $[\alpha]_D=-14.5°$ (c=0.4/H$_2$O) (30° C.)

Infrared absorption frequencies (I.R.) (cm$^{-1}$) 3450, 2930, 2850, 1720, 1610, 1500, 1260, 1120, 1080, 990, 800

PMR spectra (D$_2$O) (ppm) 0.82(3H) 1.10–1.30(18H) 1.45–1.55(2H) 3.4–5.5 6.9–7.2(6.2H) 7.9–8.15(3.1H)

The percent of acyl groups in the compound to be calculated from the PMR data: 19%.

The percent of sulfate groups in the compound to be calculated from the elementary analysis value: 64%.

COMPOUND EXAMPLE 7

Synthesis of Sulfated n-dodecyl O-2,4-difluorobenzoyl-β-D-laminaripentaoside (2): (Compound 7)

By using 170 mg of 2,4-difluorobenzoyl chloride, 680 mg of n-dodecyl O-2,4-difluorobenzoyl-β-D-laminaripentaoside was prepared from 600 mg of n-dodecyl β-D-laminaripentaoside. The difluorobenzoate (400 mg) was reacted with 570 mg of sulfur trioxide pyridine complex, in a manner similar to that for COMPOUND EXAMPLE 1. The yield of the target compound was 602 mg.

Specific rotation: $[\alpha]_D=-6.4°$ (c=0.45/H$_2$O) (30° C.)

Infrared absorption frequencies (I.R.) (cm$^{-1}$) 3400, 3050, 2930, 2850, 1710, 1610, 1510, 1260, 1120, 1070, 800

PMR spectra (D$_2$O) (ppm) 0.85(3H) 1.15–1.30(18H) 1.50–1.60(2H) 3.4–5.5 7.1–7.25(4.6H) 8.0–8.2(2.3H)

The percent of acyl groups in the compound to be calculated from the PMR data: 14%.

The percent of sulfate groups in the compound to be calculated from the elementary analysis value: 62%.

COMPOUND EXAMPLE 8

Synthesis of Sulfated 4-n-octylphenyl O-benzoyl-β-D-laminaripentaoside: (Compound 8)

4-n-octylphenyl β-D-laminaripentaoside was synthesized by using the similar method of REFERENCE SYNTHESIS EXAMPLE 1.

Specific rotation of 4-n-octylphenyl β-D-laminaripentaoside: $[\alpha]\beta_D=+0.74°$ (c=0.4/MeOH) (30° C.)

By using 500 mg of benzoyl chloride, 1.72 g of 4-n-octylphenyl O-benzoyl-β-D-laminaripentaoside was prepared from 1.01 g of 4-n-octylphenyl β-D-laminaripentaoside. The benzoate (520 mg) was reacted with 980 mg of sulfur trioxide pyridine complex, in a manner similar to that for COMPOUND EXAMPLE 1. The yield of the target compound was 682 mg.

Specific rotation: $[\alpha]_D=-14.1°$ (c=0.41/H$_2$O) (30° C.)

PMR spectra (D$_2$O) (ppm) 0.8–0.9 1.0–2.5 3.5–5.5 7.07 (2H) 7.18(2H) 7.4–7.7(14.9H) 7.9–8.2(9.9H)

The percent of acyl groups in the compound to be calculated from the PMR data: 31%.

The percent of sulfate groups in the compound to be calculated from the elementary analysis value: 61%.

COMPOUND EXAMPLE 9

Synthesis of Sulfated 4-n-octylphenyl O-4-fluorobenzoyl-β-D-laminaripentaoside 1: (Compound 9)

By using 570 mg of 4-fluorobenzoyl chloride, 175 g of 4-n-octylphenyl O-4-fluorobenzoyl-β-D-laminaripentaoside was prepared from 1.00 g of 4-n-octylphenyl β-D-laminaripentaoside.

Specific rotation of 4-n-octylphenyl O-4-fluorobenzoyl-β-D-laminaripentaoside: $[\alpha]_D=+6.2°$ (c=0.46/Pyridine) (30° C.)

The benzoate (500 mg) was reacted with 864 mg of sulfur trioxide pyridine complex, in a manner similar to that for COMPOUND EXAMPLE 1. The yield of the target compound was 663 mg.

Specific rotation: $[\alpha]_D=-9.9°$ (c=0.42/H$_2$O) (29° C.)

PMR spectra (D$_2$O) (ppm) 0.8–0.9(3H) 1.0–2.5 3.5–5.5 7.0–7.4(16.5H) 7.8–8.3(12.5H)

The percent of acyl groups in the compound to be calculated from the PMR data: 39%.

The percent of sulfate groups in the compound to be calculated from the elementary analysis value: 41%.

COMPOUND EXAMPLE 10

Synthesis of Sulfated 4-n-octylphenyl O-2,4-difluorobenzoyl-β-D-laminaripentaoside: (Compound 10)

By using 270 mg of 2,4-difluorobenzoyl chloride, 785 mg of 4-n-octylphenyl O-2,4-difluorobenzoyl-β-D-laminaripentaoside was prepared from 600 mg of 4-n-octylphenyl β-D-laminaripentaoside.

The 2,4-difluorobenzoate (400 mg) was reacted with 970 mg of sulfur trioxide pyridine complex, in a manner similar to that for COMPOUND EXAMPLE 1. The yield of the target compound was 602 mg.

Specific rotation: $[\alpha]_D=-9.2°$ (c=0.63/H$_2$O) (33° C.)

PMR spectra (D$_2$O) (ppm) 0.8–0.9(3H) 1.0–2.5 3.5–5.5 6.8–7.4 7.8–8.3(4.6H)

The percent of acyl groups in the compound to be calculated from the PMR data: 29%.

The percent of sulfate groups in the compound to be calculated from the elementary analysis value: 46%.

COMPOUND EXAMPLE 11

Synthesis of Sulfated 4-n-octyloxyphenyl O-benzoyl-β-D-laminaripentaoside: (compound 11)

4-n-octyloxyphenyl β-D-laminaripentaoside was synthesized by using the method of REFERENCE SYNTHESIS EXAMPLE 1.

Specific rotation of 4-n-octyloxyphenyl β-D-laminaripentaoside: $[\alpha]_D=-4.1°$ (c=0.42/MeOH) (30° C.)

By using 560 mg of benzoyl chloride, 1.03 g of 4-n-octyloxyphenyl O-benzoyl-β-D-laminaripentaoside was prepared from 1.00 g of 4-n-octyloxyphenyl β-D-laminaripentaoside.

Specific rotation of the intermediate: 4-n-octyloxyphenyl O-benzoyl-β-D-laminaripentaoside: $[\alpha]_D=+3.6°$ (c=0.40/Pyridine) (27° C.)

The benzoate (600 mg) was reacted with 1.58 g of sulfur trioxide pyridine complex, in a manner similar to that for COMPOUND EXAMPLE 1. The yield of the target compound was 744 mg.

Specific rotation: $[\alpha]_D=-19.5°$ (c=0.48/H$_2$O) (30° C.)

PMR spectra (D$_2$O) (ppm) 0.8–0.9(3H) 1.0–2.5 3.5–5.5 7.0–7.7 7.8–8.3(9.6H)

The percent of acyl groups in the compound to be calculated from the PMR data: 30%.

The percent of sulfate groups in the compound to be calculated from the elementary analysis value: 51%.

COMPOUND EXAMPLE 12

Synthesis of Sulfated 4-n-octyloxyphenyl O-4-fluorobenzoyl-β-D-laminaripentaoside: (Compound 12)

By using 760 mg of 4-fluorobenzoyl chloride, 1.20 g of 4-n-octyloxyphenyl O-4-fluorobenzoyl-β-D-laminaripentaoside was prepared from 1.00 g of 4-n-octyloxyphenyl β-D-laminaripentaoside.

Specific rotation of intermediate: 4-n-octyloxyphenyl O-4-fluorobenzoyl-β-D-laminaripentaoside: $[\alpha]_D=-22.6°$ (c=0.67/Pyridine) (30° C.)

The fluorobenzoate (700 mg) was reacted with 2.07 g of sulfur trioxide pyridine complex, in a manner similar to that for COMPOUND EXAMPLE 1. The yield of the target compound was 460 mg.

Specific rotation: $[\alpha]_D=-19.2°$ (c=0.51/H$_2$O) (33° C.)

PMR spectra (D$_2$O) (ppm) 0.8–0.9(3H) 1.0–2.5 3.5–5.5 7.0–7.4(12H) 7.8–8.3(8H)

The percent of acyl groups in the compound to be calculated from the PMR data: 25%.

The percent of sulfate groups in the compound to be calculated from the elementary analysis value: 59%.

COMPOUND EXAMPLE 13

Synthesis of Sulfated 4-n-octyloxyphenyl O-2,4-difluorobenzoyl-β-D-laminaripentaoside: (Compound 13)

By using 170 mg of 2,4-difluorobenzoyl chloride, 680 mg of 4-n-octyloxyphenyl O-2,4-difluorobenzoyl-β-D-laminaripentaoside was prepared from 600 mg of 4-n-octyloxyphenyl β-D-laminaripentaoside.

The 2,4-difluorobenzoate (400 mg) was reacted with 570 mg of sulfur trioxide pyridine complex, in a manner similar to that for COMPOUND EXAMPLE 1. The yield of the target compound was 602 mg.

Specific rotation: $[\alpha]_D=-10.3°$ (c=0.69/H$_2$O) (33° C.)

PMR spectra (D$_2$O) (ppm) 0.8–0.9(3H) 1.0–2.5 3.5–5.5 7.0–7.4(14.8H) 7.8–8.3(5.4H)

The percent of acyl groups in the compound to be calculated from the PMR data: 34%.

The percent of sulfate groups in the compound to be calculated from the elementary analysis value: 47%.

COMPOUND EXAMPLE 14

Synthesis of Sulfated 4-t-octylphenyl O-benzoyl-β-D-laminaripentaoside: (Compound 14)

4-t-octylphenyl β-D-laminaripentaoside was synthesized by using the similar method of REFERENCE SYNTHESIS EXAMPLE 1.

Specific rotation of 4-t-octylphenyl β-D-laminaripentaoside: $[\alpha]_D=-0.1°$ (c=0.35/MeOH) (30° C.)

By using 570 mg of benzoyl chloride and 4.74 g of sulfur trioxide pyridine complex, 1.36 g of sulfated 4-t-octylphenyl O-benzoyl-β-D-laminaripentaoside was prepared from 1.50 g of 4-t-octylphenyl β-D-laminaripentaoside, in a manner similar to that for COMPOUND EXAMPLE 1.

Specific rotation of the intermediate: 4-t-octylphenyl O-benzoyl-β-D-laminaripentaoside: $[\alpha]_D=-0.32°$ (c=0.41/Pyridine) (25° C.)

Specific rotation: $[\alpha]_D=-13.2°$ (c=0.41/H$_2$O) (30° C.)

PMR spectra (D$_2$O) (ppm) 0.8–0.9 1.2–2.5 3.9–5.4 6.96(2H) 7.13 7.3–7.7 7.8–8.3(14.1H)

The percent of acyl groups in the compound to be calculated from the PMR data: 44%.

The percent of sulfate groups in the compound to be calculated from the elementary analysis value: 42%.

COMPOUND EXAMPLE 15

Synthesis of Sulfated 4-t-octylphenyl O-4-fluorobenzoyl-β-D-laminaripentaoside: (Compound 15)

By using 580 mg of 4-fluorobenzoyl chloride and 5.53 g of sulfur trioxide pyridine complex, 1.16 g of sulfated 4-t-octylphenyl O-benzoyl-β-D-laminaripentaoside was prepared from 1.00 g of 4-t-octylphenyl β-D-laminaripentaoside, in a manner similar to that for COMPOUND EXAMPLE 1.

Specific rotation of the intermediate: 4-t-octylphenyl O-4-fluorobenzoyl-β-D-laminaripentaoside: $[\alpha]_D=+6.2°$ (c=0.46/Pyridine) (30° C.)

Specific rotation: $[\alpha]_D=-23.3°$ (c=0.42/H$_2$O) (30° C.)

PMR spectra (D$_2$O) (ppm) 0.8–0.9(9H) 1.1–2.5 3.9–5.4 6.9–7.4 7.8–8.3(10.9H)

The percent of acyl groups in the compound to be calculated from the PMR data: 34%.

The percent of sulfate groups in the compound to be calculated from the elementary analysis value: 49%.

COMPOUND EXAMPLE 16

Synthesis of Sulfated 4-t-octylphenyl O-2,4-difluorobenzoyl-β-D-laminaripentaoside: (Compound 16)

By using 600 mg of 2,4-difluorobenzoyl chloride and 2.50 g of sulfur trioxide pyridine complex, 2.39 g of sulfated 4-t-octylphenyl O-2,4-difluorobenzoyl-β-D-laminaripentaoside was prepared from 1.00 g of 4-t-octylphenyl β-D-laminaripentaoside, in a manner similar to that for COMPOUND EXAMPLE 1.

Specific rotation of the intermediate: 4-t-octylphenyl O-2,4-difluorobenzoyl-β-D-laminaripentaoside: $[\alpha]_D=-1.2°$ (c=0.66/Pyridine) (30° C.)

Specific rotation: $[\alpha]_D=-7.6°$ (c=0.62/H$_2$O) (33° C.)

PMR spectra (DMSO-d$_6$/D$_2$O) (ppm) 0.8–0.9(9H) 1.1–2.5 3.9–5.4 6.8–7.4 7.8–8.3(13.8H)

The percent of acyl groups in the compound to be calculated from the PMR data: 43%.

The percent of sulfate groups in the compound to be calculated from the elementary analysis value: 44%.

COMPOUND EXAMPLE 17

Synthesis of Sulfated 4-t-octylphenyl O-benzoyl-β-D-galactosyl-(1→4)-β-D-galactosyl-(1→4)-β-D-glucoside: (Compound 17)

4-t-octylphenyl β-D-galactosyl-(1→4)-β-D-galactosyl(1→4)-β-D-glucoside was synthesized by using the similar method of REFERENCE SYNTHESIS EXAMPLE 1.

Specific rotation of 4-t-octylphenyl β-D-galactosyl-(1→4)-β-D-galactosyl-(1→4)-β-D-glucoside: $[\alpha]_D=-3.6°$ (c=0.55/MeOH) (29° C.)

By using 150 mg of benzoyl chloride and 1.09 g of sulfur trioxide pyridine complex, 914 mg of sulfated 4-t-octylphenyl O-benzoyl-β-D-galactosyl-(1→4)-β-D-galactosyl(1→4)-β-D-glucoside was prepared from 300 mg of 4-t-octylphenyl β-D-galactosyl-(1→4)-β-D-galactosyl-(1→4)-β-D-glucoside, in a manner similar to that for COMPOUND EXAMPLE 1.

Specific rotation of the intermediate: 4-t-octylphenyl O-benzoyl-β-D-galactosyl-(1→4)-β-D-galactosyl-(1→4)-β-D-glucoside: $[\alpha]_D=+49.6°$ (c=0.41/Pyridine) (27° C.)

Specific rotation: $[\alpha]_D=+17.0°$ (c=0.50/H$_2$O) (28° C.)

PMR spectra (D$_2$O) (ppm) 0.8–0.9(9H) 1.1–2.5 3.9–5.4 6.8–7.6 7.8–8.3(6.2H)

The percent of acyl groups in the compound to be calculated from the PMR data: 31%.

The percent of sulfate groups in the compound to be calculated from the elementary analysis value: 40%.

COMPOUND EXAMPLE 18

Synthesis of Sulfated 4-n-heptylphenyl O-benzoyl-β-D-galactosyl-(1→4)-β-D-galactosyl-(1→4)-β-D-glucoside: (Compound 18)

4-n-heptylphenyl β-D-galactosyl-(1→4)-β-D-galactosyl-(1→4)-β-D-glucoside was synthesized by using the similar method of REFERENCE SYNTHESIS EXAMPLE 1.

Specific rotation of 4-n-heptylphenyl β-D-galactosyl-(1→4)-β-D-galactosyl-(1→4)-β-D-glucoside: $[\alpha]_D=-2.0°$ (c=0.53/MeOH) (29° C.)

By using 150 mg of benzoyl chloride and 571 mg of sulfur trioxide pyridine complex, 554 mg of the sulfated 4-n-heptylphenyl O-benzoyl-β-D-galactosyl-(1→4)-β-D-galactosyl(1→4)-β-D-glucoside was prepared from 300 mg of 4-n-heptylphenyl β-D-galactosyl-(1→4)-β-D-galactosyl-(1→4)-β-D-glucoside, in a manner similar to that for COMPOUND EXAMPLE 1.

Specific rotation of the intermediate: 4-n-heptylphenyl O-benzoyl-β-D-galactosyl-(1→4)-β-D-galactosyl-(1→4)-β-D-glucoside: $[\alpha]_D=+40.6°$ (c=0.43/Pyridine) (28° C.)

Specific rotation: $[\alpha]_D=+15.9°$ (c=0.38/H$_2$O) (28° C.)

PMR spectra (D$_2$O) (ppm) 0.8–0.9(3H) 1.1–2.5 3.6–5.5 6.9–7.6 7.8–8.3(6H)

The percent of acyl groups in the compound to be calculated from the PMR data: 30%.

The percent of sulfate groups in the compound to be calculated from the elementary analysis value: 52%.

COMPOUND EXAMPLE 19

Synthesis of Sulfated 4-n-butoxyphenyl O-hexadecyl-β-D-galactosyl-(1→4)-β-D-galactosyl-(1→4)-β-D-glucoside: (Compound 19)

4-n-butoxyphenyl β-D-galactosyl-(144)-β-D-galactosyl(1→4)-β-D-glucoside was synthesized by using the similar method of REFERENCE SYNTHESIS EXAMPLE 1.

Specific rotation of 4-n-butoxylphenyl β-D-galactosyl- (1→4)-β-D-galactosyl-(1→4)-β-D-glucoside: $[\alpha]_D=-3.5°$ (c=0.51/MeOH) (29° C.)

By using 165 mg of n-hexadecanoyl chloride and 690 mg of sulfur trioxide pyridine complex, 495 mg of sulfated 4-n-butoxyphenyl O-n-hexadecanoyl-β-D-galactosyl-(1→4)-β-D-galactosyl-(1→4)-β-D-glucoside was prepared from 350 mg of 4-n-butoxyphenyl β-D-galactosyl-(1→4)-β-D-galactosyl-(1→4)-β-D-glucoside, in a manner similar to that for COMPOUND EXAMPLE 1.

Specific rotation: $[\alpha]_D=+10.4°$ (c=0.25/H$_2$O) (28° C.)

PMR spectra (D$_2$O) (ppm) 0.8–0.9(7.5H) 1.0–2.5 3.5–5.5 6.9–7.3(4H)

The percent of acyl groups in the compound to be calculated from the PMR data: 15%.

The percent of sulfate groups in the compound to be calculated from the elementary analysis value: 60%.

COMPOUND EXAMPLE 20

Synthesis of Sulfated n-docosyl O-benzoyl-β-D-laminaripentaoside: (Compound 20)

n-Docosyl β-D-laminaripentaoside was synthesized by using the similar method of REFERENCE SYNTHESIS EXAMPLE 1.

Specific rotation of n-docosyl β-D-laminaripentaoside: $[\alpha]_D=-11.3°$ (c=0.53/MeOH) (28° C.)

By using 350 mg of benzoyl chloride, 585 mg of the n-docosyl O-benzoyl-β-D-laminaripentaoside was prepared from 680 mg of n-docosyl β-D-laminaripentaoside. The benzoate (477 mg) was reacted with 1.45 g of sulfur trioxide pyridine complex, in a manner similar to that for COMPOUND EXAMPLE 1. The yield of the target compound was 811 mg.

Specific rotation: $[\alpha]_D=-4.6°$ (c=0.60/H$_2$O) (30° C.)

PMR spectra (D$_2$O) (ppm) 0.8–0.9(3H) 1.1–2.5 3.6–5.4 7.3–7.7 7.8–8.3(8.3H)

The percent of acyl groups in the compound to be calculated from the PMR data: 26%.

The percent of sulfate groups in the compound to be calculated from the elementary analysis value: 44%.

COMPOUND EXAMPLE 21

Synthesis of Sulfated n-hexadecyl O-4-fluorobenzoyl-β-D-laminaripentaoside: (Compound 21)

n-Hexadecyl β-D-laminaripentaoside was synthesized by using the similar method of REFERENCE SYNTHESIS EXAMPLE 1.

Specific rotation of n-hexadecyl β-D-laminaripentaoside: $[\alpha]_D=-13.3°$ (c=0.50/MeOH) (28° C.)

By using 370 mg of 4-fluorobenzoyl chloride, 570 mg of n-hexadecyl O-4-fluorobenzoyl-β-D-laminaripentaoside was prepared from 490 mg of n-hexadecyl β-D-laminaripentaoside. The 4-fluorobenzoate (400 mg) was reacted with 1.57 g of sulfur trioxide pyridine complex, in a manner similar to that for COMPOUND EXAMPLE 1. The yield of the target compound was 602 mg.

Specific rotation: $[\alpha]_D=-3.6°$ (c=0.52/H$_2$O) (33° C.)

PMR spectra (DMSO-d$_6$/D$_2$O) (ppm) 0.8–0.9(3H) 1.1–1.8 3.7–5.4 7.0–7.4 7.8–8.3(6.4H)

The percent of acyl groups in the compound to be calculated from the PMR data: 20%.

The percent of sulfate groups in the compound to be calculated from the elementary analysis value: 61%.

COMPOUND EXAMPLE 22

Synthesis of Sulfated n-hexadecyl O-4-pentylbenzoyl-β-D-laminaripentaoside: (Compound 22)

By using 340 mg of 4-pentylbenzoyl chloride, 605 mg of n-hexadecyl O-4-pentylbenzoyl-β-D-laminaripentaoside was prepared from 510 mg of n-hexadecyl β-D-laminaripentaoside.

The 4-pentylbenzoate (400 mg) was reacted with 570 mg of sulfur trioxide pyridine complex, in a manner similar to that for COMPOUND EXAMPLE 1. The yield of the target compound was 602 mg.

Specific rotation: $[\alpha]_D=-4.4°$ (c=0.35/H$_2$O) (30° C.)

PMR spectra (D$_2$O) (ppm) 0.8–0.9(13.6H) 1.1–2.5 3.6–5.4 7.0–8.3(14.1H)

The percent of acyl groups in the compound to be calculated from the PMR data: 22%.

The percent of sulfate groups in the compound to be calculated from the elementary analysis value: 41%.

COMPOUND EXAMPLE 23

Synthesis of Sulfated n-dodecyl O-4-n-butoxybenzoyl-β-D-laminaripentaoside: (Compound 23)

By using 440 mg of 4-n-butoxybenzoyl chloride, 740 mg of n-dodecyl O-4-n-butoxybenzoyl-β-D-laminaripentaoside was prepared from 620 mg of n-dodecyl β-D-laminaripentaoside.

The n-butoxybenzoate (700 mg) was reacted with 2.25 g of sulfur trioxide pyridine complex, in a manner similar to that for COMPOUND EXAMPLE 1. The yield of the target compound was 910 mg.

Specific rotation: $[\alpha]_D=-6.8°$ (c=0.32/H$_2$O) (30° C.)

PMR spectra (D$_2$O) (ppm) 0.8–0.9(3.6H) 1.1–2.0 3.6–5.4 6.9–7.2(2H) 7.7–8.3(2H)

The percent of acyl groups in the compound to be calculated from the PMR data: 32%.

The percent of sulfate groups in the compound to be calculated from the elementary analysis value: 53%.

COMPOUND EXAMPLE 24

Synthesis of Sulfated 4-n-octylphenyl O-butyryl-β-D-laminari-trioside: (Compound 24)

4-n-Octylphenyl β-D-laminari-trioside was synthesized by using the similar method of REFERENCE SYNTHESIS EXAMPLE 1.

Specific rotation of peracetyl 4-n-octylphenyl β-D-laminari-trioside: $[\alpha]_D=-53.1°$ (c=1.0/CHCl$_3$) (31° C.)

Specific rotation of 4-n-octylphenyl β-D-laminari-trioside: $[\alpha]_D=-7.1°$ (c=1.1/MeOH) (32° C.)

By using 97 mg of butyryl chloride and 697 mg of sulfur trioxide pyridine complex, 680 mg of sulfated 4-n-octylphenyl O-butyryl-β-D-laminari-trioside was prepared from 217 mg of 4-n-octylphenyl β-D-laminari-trioside, in a manner similar to that for COMPOUND EXAMPLE 1.

Specific rotation: $[\alpha]_D=-11.6°$ (c=0.48/H$_2$O) (28° C.)

PMR spectra (D$_2$O) (ppm) 0.8–0.9(12.6H) 1.2–1.3 1.5–1.6 2.3–2.6 3.5–5.5 7.07(2H) 7.18(2H)

The percent of acyl groups in the compound to be calculated from the PMR data: 32%.

The percent of sulfate groups in the compound to be calculated from the elementary analysis value: 53%.

COMPOUND EXAMPLE 25

Synthesis of Sulfated 3,5,5-trimethyl-hexyl O-benzoyl-β-D-laminari-hexaoside: (Compound 25)

3,5,5-trimethyl-hexyl-β-D-laminari-hexaoside was synthesized by using the similar method of REFERENCE SYNTHESIS EXAMPLE 1.

Specific rotation of peracetyl 3,5,5-trimethyl-hexyl-β-D-laminari-hexaoside: $[\alpha]_D$=−53.7° (c=1.95/CHCl$_3$) (28° C.)

Specific rotation of 3,5,5-trimethyl-hexyl-β-D-laminari-hexaoside: $[\alpha]_D$=+14.9° (c=0.40/pyridine) (26° C.)

By using 63 mg of benzoyl chloride and 481 mg of sulfur trioxide pyridine complex, 254 mg of sulfated 3,5,5-trimethyl-hexyl O-benzoyl-β-D-laminari-hexaoside was prepared from 121 mg of 3,5,5-trimethyl-hexyl β-D-laminari-hexaoside, in a manner similar to that for COMPOUND EXAMPLE 1.

Specific rotation: $[\alpha]_D$=−24.1° (c=0.36/H$_2$O) (30° C.)

PMR spectra (D$_2$O) (ppm) 0.75–0.93(12H) 1.0–1.7 3.6–5.4 7.3–8.2(23.7H)

The percent of acyl groups in the compound to be calculated from the PMR data: 25%.

The percent of sulfate groups in the compound to be calculated from the elementary analysis value: 60%.

COMPOUND EXAMPLE 26

Synthesis of Sulfated 4-n-octyloxyphenyl O-octanoyl-β-D-laminaripentaoside: (Compound 26)

By using 390 mg of n-octanoyl chloride and 1.68 g of sulfur trioxide pyridine complex, 0.53 g of sulfated 4-n-octyloxyphenyl O-n-octanoyl-β-D-laminaripentaoside was prepared from 0.50 g of 4-n-octyloxyphenyl β-D-laminaripentaoside, in a manner similar to that for COMPOUND EXAMPLE 1.

Specific rotation: $[\alpha]_D$=−16.9° (c=0.63/H$_2$O) (31° C.)

PMR spectra (D$_2$O) (ppm) 0.76(6.2H) 0.91(3H) 1.20–2.5 3.5–5.5 7.08(2H) 7.43(2H)

The percent of acyl groups in the compound to be calculated from the PMR data: 13%.

The percent of sulfate groups in the compound to be calculated from the elementary analysis value: 77%.

COMPOUND EXAMPLE 27

Synthesis of Sulfated 4-t-octylphenyl O-n-octanoyl-β-D-laminaripentaoside: (Compound 27)

By using 399 mg of n-octanoyl chloride and 1.72 g of sulfur trioxide pyridine complex, 0.79 g of sulfated 4-t-octylphenyl O-n-octanoyl-β-D-laminaripentaoside was prepared from 0.50 g of 4-t-octylphenyl β-D-laminaripentaoside, in a manner similar to that for COMPOUND EXAMPLE 1.

Specific rotation: $[\alpha]_D$=−16.3° (c=0.72/H$_2$O) (31° C.)

PMR spectra (D$_2$O) (ppm) 0.8–0.9(22.4H) 1.2–2.5 3.9–5.4 6.95(2H) 7.13(2H)

The percent of acyl groups in the compound to be calculated from the PMR data: 28%.

The percent of sulfate groups in the compound to be calculated from the elementary analysis value: 59%.

COMPOUND EXAMPLE 28

Synthesis of Sulfated 4-n-hexylphenyl O-n-octanoyl-β-D-laminari-undecaoside: (Compound 28)

4-n-Hexylphenyl β-D-laminari-undecaoside was synthesized by using the similar method of REFERENCE SYNTHESIS EXAMPLE 1.

Specific rotation of peracetyl 4-n-hexylphenyl β-D-laminari-undecaoside: $[\alpha]_D$=−27.7° (c=1.1/CHCl$_3$) (31° C.)

Specific rotation of 4-n-hexylphenyl β-D-laminari-undecaoside: $[\alpha]_D$=−2.1° (c=1.27/DMF) (32° C.)

By using 121 mg of n-octanoyl chloride and 473 mg of sulfur trioxide pyridine complex, 257 mg of sulfated 4-n-hexylphenyl O-n-octanoyl-β-D-laminari-undecaoside was prepared from 127 mg of 4-n-hexylphenyl β-D-laminari-undecaoside, in a manner similar to that for COMPOUND EXAMPLE 1.

Specific rotation: $[\alpha]_D$=−11.3° (c=0.49/H$_2$O) (29° C.)

PMR spectra (D$_2$O) (ppm) 0.8–0.9(17.3H) 1.2–2.5 3.4–5.5 7.0–7.3(4H)

The percent of acyl groups in the compound to be calculated from the PMR data: 14%.

The percent of sulfate groups in the compound to be calculated from the elementary analysis value: 72%.

COMPOUND EXAMPLE 29

Synthesis of Sulfated 4-n-hexylphenyl O-n-octanoyl-β-D-maltohexaoside: (Compound 29)

4-n-Hexylphenyl β-D-maltohexaoside was synthesized by using the similar method of REFERENCE SYNTHESIS EXAMPLE 1. Specific rotation of peracetyl 4-n-hexylphenyl β-D-maltohexaoside: $[\alpha]_D$=+110.8° (c=0.49/CHCl$_3$) (26° C.)

Specific rotation of 4-n-hexylphenyl β-D-maltohexaoside: $[\alpha]_D$=+112.0° (c=0.55/MeOH) (30° C.)

By using 710 mg of n-octanoyl chloride and 2.31 g of sulfur trioxide pyridine complex, 850 mg of sulfated 4-n-hexylphenyl O-n-octanoyl-β-D-maltohexaoside was prepared from 790 mg of 4-n-hexylphenyl β-D-maltohexaoside, in a manner similar to that for COMPOUND EXAMPLE 1.

Specific rotation: $[\alpha]_D$=+38.6° (c=0.54/H$_2$O) (29° C.)

PMR spectra (D$_2$O) (ppm) 0.87–0.90(16H) 1.1–1.8 2.2–2.7 3.8–5.6 7.0–7.3 (4.0H)

The percent of acyl groups in the compound to be calculated from the PMR data: 27%.

The percent of sulfate groups in the compound to be calculated from the elementary analysis value: 58%.

REFERENCE SYNTHESIS EXAMPLE 2

Synthesis of dl-α-tocopheryl β-D-laminaripentaoside

In an atmosphere of argon, 139 g of the peracetyl laminaripentaose and 77.5 g of dl-α-tocopherol were dissolved in 1000 ml of dichloromethane in a 2 liter three-necked flask, to which 20 g of trimethylsilyl tri-fluoromethanesulfonate was added with agitation, over a 30 min period, while maintaining the reaction temperature between −5° and 0° C. After 16 hours agitation at 0° C., 11.3 ml of triethylamine was added to the reaction mixture with keeping the temperature at −5° C. The reaction mixture was diluted with 1000 ml of dichloromethane, washed with three times with 500 ml portions of saturated sodium bicarbonate solution and with two times with 500 ml portions of saturated sodium chloride solution. The dichloromethane solution was dried with anhydrous sodium sulfate, evaporated to dryness. This crude product was refined by silica gel column chromatography (ethyl acetate and hexane). The yield was 120 g (69%).

Specific rotation of peracetyl dl-α-tocopheryl β-D-laminari-pentaoside: $[\alpha]_D=-41.8°$ (c=1.1/CHCl$_3$) (30° C.)

Deacetylation was carried out with the similar method of REFERENCE SYNTHESIS EXAMPLE 1.

Specific rotation of dl-α-tocopheryl β-D-laminaripentaoside: $[\alpha]_D=-19.1°$ (c=0.56/pyridine) (30° C.)

COMPOUND EXAMPLE 30

Synthesis of Sulfated dl-α-tocopheryl O-n-butyryl-β-D-laminaripentaoside (1): (Compound 30)

By using 341 mg of n-butyryl chloride and 7.13 g of sulfur trioxide pyridine complex, 3.13 g of sulfated dl-α-tocopheryl O-n-butyryl-β-D-laminaripentaoside was prepared from 2.01 g of dl-α-tocopheryl β-D-laminaripentaoside, in a manner similar to that for COMPOUND EXAMPLE 1.

Specific rotation of the intermediate: dl-α-tocopheryl O-n-butyryl-β-D-laminaripentaoside: $[\alpha]_D=-13.9°$ (c=0.49/pyridine) (30° C.)

Specific rotation: $[\alpha]_D=-17.8°$ (c=1.06/H$_2$O) (29° C.)

PMR spectra (DMSO-d$_6$) (ppm) 0.82–0.86(18.2H) 1.0–1.6 1.73(2H) 2.0–2.4 3.8–5.3

The percent of acyl groups in the compound to be calculated from the PMR data: 13%.

The percent of sulfate groups in the compound to be calculated from the elementary analysis value: 71%.

COMPOUND EXAMPLE 31

Synthesis of Sulfated dl-α-tocopheryl O-n-butyryl-β-D-laminaripentaoside (2): (Compound 31)

By using 700 mg of n-butyryl chloride and 3.92 g of sulfur trioxide pyridine complex, 2.71 g of sulfated dl-α-tocopheryl O-n-butyryl-β-D-laminaripentaoside was prepared from 2.01 g of dl-α-tocopheryl β-D-laminaripentaoside, in a manner similar to that for COMPOUND EXAMPLE 1.

Specific rotation: $[\alpha]_D=-16.5°$ (c=1.08/H$_2$O) (30° C.)

PMR spectra (DMSO-d$_6$) (ppm) 0.82–0.86(24H) 1.0–1.6 1.73(2H) 2.0–2.4 3.8–5.3

The percent of acyl groups in the compound to be calculated from the PMR data: 25%.

The percent of sulfate groups in the compound to be calculated from the elementary analysis value: 66%.

COMPOUND EXAMPLE 32

Synthesis of Sulfated dl-α-tocopheryl O-n-butyryl-β-D-laminaripentaoside: (Compound 32)

By using 1.36 g of n-butyryl chloride and 2.80 g of sulfur trioxide pyridine complex, 2.62 g of sulfated dl-α-tocopheryl O-benzoyl-β-D-laminaripentaoside was prepared from 2.01 g of dl-α-tocopheryl β-D-laminaripentaoside, in a manner similar to that for COMPOUND EXAMPLE 1.

Specific rotation: $[\alpha]_D=-16.0°$ (c=0.92/H$_2$O) (29° C.)

PMR spectra (DMSO-d$_6$) (ppm) 0.82–0.86(37.4H) 1.0–1.6 1.73(2H) 2.0–2.4 3.8–5.3

The percent of acyl groups in the compound to be calculated from the PMR data: 53%.

The percent of sulfate groups in the compound to be calculated from the elementary analysis value: 33%.

COMPOUND EXAMPLE 33

Synthesis of Sulfated dl-α-tocopheryl O-n-octanoyl-β-D-laminaripentaoside (1): (Compound 33)

By using 520 mg of octanoyl chloride and 7.13 g of sulfur trioxide pyridine complex, 3.22 g of sulfated dl-α-tocopheryl O-n-octanoyl-β-D-laminaripentaoside was prepared from 2.01 g of dl-α-tocopheryl β-D-laminaripentaoside, in a manner similar to that for COMPOUND EXAMPLE 1.

Specific rotation of the intermediate: dl-α-tocopheryl O-n-octanoyl-β-D-laminaripentaoside: $[\alpha]_D=-10.5°$ (c=0.49/pyridine) (31° C.)

Specific rotation: $[\alpha]_D=-16.6°$ (c=0.93/H$_2$O) (30° C.)

PMR spectra (DMSO-d$_6$) (ppm) 0.82–0.86(21.1H) 1.0–1.6 1.73(2H) 2.0–2.4 3.8–5.3

The percent of acyl groups in the compound to be calculated from the PMR data: 19%.

The percent of sulfate groups in the compound to be calculated from the elementary analysis value: 71%.

COMPOUND EXAMPLE 34

Synthesis of Sulfated dl-α-tocopheryl O-n-octanoyl-β-D-laminaripentaoside (2): (Compound 34)

By using 1.42 g of n-octanoyl chloride, 3.12 g of dl-α-tocopheryl O-n-octanoyl-β-D-laminaripentaoside was prepared from 2.06 g of dl-α-tocopheryl β-D-laminaripentaoside. The octanoate (3.00 g) was reacted with 4.95 g of sulfur trioxide pyridine complex, in a manner similar to that for COMPOUND EXAMPLE 1. The yield of the target compound was 3.63 g.

Specific rotation: $[\alpha]_D=-9.8°$ (c=0.44/H$_2$O) (28° C.)

PMR spectra (D$_2$O) (ppm) 0.82–0.86(26.9H) 1.0–1.6 1.73(2H) 2.0–2.4 3.8–5.3

The percent of acyl groups in the compound to be calculated from the PMR data: 31%.

The percent of sulfate groups in the compound to be calculated from the elementary analysis value: 60%.

COMPOUND EXAMPLE 35

Synthesis of Sulfated dl-α-tocopheryl O-n-octanoyl-β-D-laminaripentaoside (3): (Compound 35)

By using 2.26 g of n-octanoyl chloride, 3.02 g of dl-α-tocopheryl O-n-octanoyl-β-D-laminaripentaoside was prepared from 2.05 g of dl-α-tocopheryl β-D-laminari-pentaoside. The octanoate (2.05 g) was reacted with 3.85 g of sulfur trioxide pyridine complex, in a manner similar to that for COMPOUND EXAMPLE 1. The yield of the target compound was 2.35 g.

Specific rotation: $[\alpha]_D=-8.3°$ (c=0.48/H$_2$O) (27° C.)

PMR spectra (D$_2$O) (ppm) 0.82–0.86(44.6H) 1.0–1.6 1.73(2H) 2.0–2.4 3.8–5.3

The percent of acyl groups in the compound to be calculated from the PMR data: 68%.

The percent of sulfate groups in the compound to be calculated from the elementary analysis value: 22%.

COMPOUND EXAMPLE 36

Synthesis of Sulfated dl-α-tocopheryl O-n-dodecanoyl-β-D-laminaripentaoside (1): (Compound 36)

By using 0.77 g of n-dodecanoyl chloride, 1.82 g of dl-α-tocopheryl O-n-dodecanoyl-β-D-laminaripentaoside was prepared from 2.02 g of dl-α-tocopheryl β-D-laminaripentaoside.

The dodecanoate (1.81 g) was reacted with 2.54 g of sulfur trioxide pyridine complex, in a manner similar to that for COMPOUND EXAMPLE 1.

The yield of the target compound was 3.60 g.

Specific rotation of the intermediate: dl-α-tocopheryl O-n-dodecanoyl-β-D-laminaripentaoside: $[\alpha]_D$=–23.5° (c=0.42/pyridine) (28° C.)

Specific rotation: $[\alpha]_D$=–6.9° (c=0.61/H$_2$O) (27° C.)

PMR spectra (D$_2$O) (ppm) 0.82–0.86(24H) 1.0–1.6 1.73(2H) 2.0–2.4 3.8–5.3

The percent of acyl groups in the compound to be calculated from the PMR data: 25%.

The percent of sulfate groups in the compound to be calculated from the elementary analysis value: 62%.

COMPOUND EXAMPLE 37

Synthesis of Sulfated dl-α-tocopheryl O-n-dodecanoyl-β-D-laminaripentaoside (2): (Compound 37)

By using 0.79 g of n-dodecanoyl chloride, 1.23 g of dl-α-tocopheryl O-n-dodecanoyl-β-D-laminaripentaoside was prepared from 2.07 g of dl-α-tocopheryl β-D-laminaripentaoside.

The dodecanoate (1.22 g) was reacted with 3.39 g of sulfur trioxide pyridine complex, in a manner similar to that for COMPOUND EXAMPLE 1.

The yield of the target compound was 1.41 g.

Specific rotation: $[\alpha]_D$=–2.2° (c=0.51/H$_2$O) (26° C.)

PMR spectra (D$_2$O) (ppm) 0.82–0.86(33.1H) 1.0–1.6 1.73(2H) 2.0–2.4 3.8–5.3

The percent of acyl groups in the compound to be calculated from the PMR data: 44%.

The percent of sulfate groups in the compound to be calculated from the elementary analysis value: 45%.

COMPOUND EXAMPLE 38

Synthesis of Sulfated dl-α-tocopheryl O-n-dodecanoyl-β-D-laminaripentaoside (3): (Compound 38)

By using 1.99 g of n-dodecanoyl chloride, 2.78 g of dl-α-tocopheryl O-n-dodecanoyl-β-D-laminaripentaoside was prepared from 2.08 g of dl-α-tocopheryl β-D-laminaripentaoside.

The dodecanoate (2.70 g) was reacted with 4.51 g of sulfur trioxide pyridine complex, in a manner similar to that for COMPOUND EXAMPLE 1.

The yield of the target compound was 3.01 g.

Specific rotation: $[\alpha]_D$=–5.8° (c=0.44/H$_2$O) (27° C.)

PMR spectra (DMSO-d$_6$/D$_2$O) (ppm) 0.82–0.86(38.4H) 1.0–1.6 1.73(2H) 2.0–2.4 3.8–5.3

The percent of acyl groups in the compound to be calculated from the PMR data: 55%.

The percent of sulfate groups in the compound to be calculated from the elementary analysis value: 34%.

COMPOUND EXAMPLE 39

Synthesis of Sulfated dl-α-tocopheryl O-n-dodecanoyl-β-D-laminaripentaoside (4): (Compound 39)

By using 3.19 g of n-dodecanoyl chloride, 3.95 g of dl-α-tocopheryl O-n-dodecanoyl-β-D-laminaripentaoside was prepared from 2.08 g of dl-α-tocopheryl β-D-laminaripentaoside.

The dodecanoate (3.92 g) was reacted with 1.85 g of sulfur trioxide pyridine complex, in a manner similar to that for COMPOUND EXAMPLE 1.

The yield of the target compound was 4.39 g.

Specific rotation: $[\alpha]_D$=–7.4° (c=0.69/CH$_2$Cl$_2$) (27° C.)

PMR spectra (D$_2$O-DMSOd$_6$) (ppm) 0.82–0.86(47.5H) 1.0–1.6 1.73(2H) 2.0–2.4 3.8–5.3

The percent of acyl groups in the compound to be calculated from the PMR data: 74%.

The percent of sulfate groups in the compound to be calculated from the elementary analysis value: 21%.

COMPOUND EXAMPLE 40

Synthesis of Sulfated dl-α-tocopheryl O-n-docosanoyl-β-D-laminaripentaoside: (Compound 40)

By using 3.47 g of n-docosanoyl chloride, 3.35 g of dl-α-tocopheryl O-n-docosanoyl-β-D-laminaripentaoside was prepared from 2.03 g of dl-α-tocopheryl β-D-laminaripentaoside.

Specific rotation of the intermediate: dl-α-tocopheryl O-n-docosanoyl-β-D-laminaripentaoside: $[\alpha]_D$=–7.9° (c=0.63/pyridine) (26° C.)

The docosanoate (0.99 g) was reacted with 1.22 g of sulfur trioxide pyridine complex, in a manner similar to that for COMPOUND EXAMPLE 1.

The yield of the target compound was 1.21 g.

Specific rotation: $[\alpha]_D$=–4.2° (c=0.42/CH$_2$Cl$_2$) (30° C.)

PMR spectra (DMSO-d$_6$/H$_2$O) (ppm) 0.82–0.86(45.1H) 1.0–1.6 1.73(2H) 2.0–2.4 3.8–5.3

The percent of acyl groups in the compound to be calculated from the PMR data: 69%.

The percent of sulfate groups in the compound to be calculated from the elementary analysis value: 21%.

COMPOUND EXAMPLE 41

Synthesis of Sulfated dl-α-tocopheryl O-n-butyryl-β-D-galactosyl-(1→4)-β-D-galactosyl-(1→4)-β-D-glucoside(1): (Compound 41)

By using 0.49 g of n-butyryl chloride, 1.25 g of dl-α-tocopheryl O-n-butyryl-β-D-laminaripentaoside was prepared from 1.08 g of dl-α-tocopheryl β-D-laminaripentaoside.

Specific rotation of intermediate: dl-α-tocopheryl O-n-butyryl-β-D-galactosyl-(1→4)-β-D-galactosyl-(1→4)-β-D-glucoside: $[α]_D$=11.1° (c=0.71/pyridine) (25° C.)

The butyrate (1.06 g) was reacted with 1.94 g of sulfur trioxide pyridine complex, in a manner similar to that for COMPOUND EXAMPLE 1.

The yield of the target compound was 1.01 g.

Specific rotation: $[α]_D$=−0.48° (c=0.52/H₂O) (26° C.)

PMR spectra (D₂O) (ppm) 0.82–0.86(18.3H) 1.0–1.7 1.73(2H) 2.0–2.4 3.8–5.3

The percent of acyl groups in the compound to be calculated from the PMR data: 21%.

The percent of the sulfate groups in the compound to be calculated from the elementary analysis value: 59%.

COMPOUND EXAMPLE 42

Synthesis of Sulfated dl-α-tocopheryl O-n-butyryl-β-D-galactosyl-(1→4)-β-D-galactosyl-(1→4)-β-D-glucoside (2): (Compound 42)

By using 0.49 g of n-butyryl chloride, 1.20 g of dl-α-tocopheryl O-n-butyryl-β-D-laminaripentaoside was prepared from 1.07 g of dl-α-tocopheryl β-D-laminaripentaoside.

Specific rotation of the intermediate: dl-α-tocopheryl O-n-butyryl-β-D-galactosyl-(1→4)-β-D-galactosyl-(1→4)-β-D-glucoside: $[α]_D$=+14.2° (c=0.71/pyridine) (25° C.)

The butyrate (1.20 g) was reacted with 1.93 g of sulfur trioxide pyridine complex, in a manner similar to that for COMPOUND EXAMPLE 1.

The yield of the target compound was 1.22 g.

Specific rotation: $[α]_D$=+0.87° (c=0.56/H₂O) (27° C.)

PMR spectra (D₂O) (ppm) 0.82–0.86(18.9H) 1.0–1.7 1.73(2H) 2.0–2.4 3.8–5.3

The percent of acyl groups in the compound to be calculated from the PMR data: 23%.

The percent of the sulfate groups in the compound to be calculated from the elementary analysis value: 69%.

COMPOUND EXAMPLE 43

Synthesis of Sulfated dl-α-tocopheryl O-2,4-difluorobenzoyl-β-D-galactosyl-(1→4)-β-D-galactosyl-(1→4)-β-D-glucoside: (Compound 43)

By using 0.41 g of 2,4-n-difluorobenzoyl chloride, 1.06 g of dl-α-tocopheryl O-2,4-difluorobenzoyl-β-D-galactosyl-(1→4)-β-D-galactosyl-(1→4)-β-D-glucoside was prepared from 1.01 g of dl-α-tocopheryl β-D-β-D-galactosyl-(1→4)-β-D-galactosyl-(1→4)-β-D-glucoside.

Specific rotation of the intermediate: dl-α-tocopheryl O-2,4-difluorobenzoyl-β-D-β-D-galactosyl-(1→4)-β-D-galactosyl-(1→4)-β-D-glucoside: $[α]_D$=+11.4° (c=0.62/pyridine) (26° C.)

The 2,4-difluorobenzoate (0.93 g) was reacted with 2.15 g of sulfur trioxide pyridine complex, in a manner similar to that for COMPOUND EXAMPLE 1. The yield of the target compound was 1.23 g.

Specific rotation: $[α]_D$=+3.58° (c=0.45/H₂O) (26° C.)

PMR spectra (D₂O) (ppm) 0.82–0.86(5.7H) 1.0–1.6 2.0–2.5 3.8–5.3 7.0–7.2(2H) 7.8–8.3(1H)

The percent of acyl groups in the compound to be calculated from the PMR data: 21%.

The percent of the sulfate groups in the compound to be calculated from the elementary analysis value: 69%.

COMPOUND EXAMPLE 44

Synthesis of Sulfated dl-α-tocopheryl O-benzoyl-β-D-laminaripentaoside (1): (Compound 44)

By using 190 mg of benzoyl chloride and 3.57 g of sulfur trioxide pyridine complex, 1.81 g of sulfated dl-α-tocopheryl O-benzoyl-β-D-laminaripentaoside was prepared from 1.00 g of dl-α-tocopheryl β-D-laminaripentaoside, in a manner similar to that for COMPOUND EXAMPLE 1.

Specific rotation: $[α]_D$=−16.2° (c=0.42/H₂O) (30° C.)

PMR spectra (D₂O) (ppm) 0.82–0.86(5.4H) 1.0–1.6 1.7–2.5 3.8–5.5 7.2–7.8(3H) 7.9–8.3(2H)

The percent of acyl groups in the compound to be calculated from the PMR data: 14%.

The percent of sulfate groups in the compound to be calculated from the elementary analysis value: 68%.

COMPOUND EXAMPLE 45

Synthesis of Sulfated dl-α-tocopheryl O-benzoyl-β-D-laminaripentaoside (2): (Compound 45)

By using 460 mg of benzoyl chloride and 707 mg of sulfur trioxide pyridine complex, 468 mg of sulfated dl-α-tocopheryl O-benzoyl-β-D-laminaripentaoside was prepared from 1.00 g of dl-α-tocopheryl β-D-laminaripentaoside, in a manner similar to that for COMPOUND EXAMPLE 1.

Specific rotation: $[α]_D$=−20.8° (c=0.454/H₂O) (30° C.)

PMR spectra (D₂O) (ppm) 0.82–0.86(3.3H) 1.0–116 1.7–2.5 3.8–5.5 7.2–7.8(3H) 7.9–8.3(2H)

The percent of acyl groups in the compound to be calculated from the PMR data: 23%.

The percent of sulfate groups in the compound to be calculated from the elementary analysis value: 55%.

COMPOUND EXAMPLE 46

Synthesis of Sulfated dl-α-tocopheryl O-benzoyl-β-D-laminaripentaoside (3): (Compound 46)

By using 740 mg of benzoyl chloride and 1.10 g of sulfur trioxide pyridine complex, 1.21 g of sulfated dl-α-tocopheryl O-benzoyl-β-D-laminaripentaoside was prepared from 1.00 g of dl-α-tocopheryl β-D-laminaripentaoside, in a manner similar to that for COMPOUND EXAMPLE 1.

Specific rotation: $[α]_D$=−18.0° (c=0.78/H₂O) (31° C.)

PMR spectra (D₂O) (ppm) 0.82–0.86(2.3H) 1.0–1.6 1.7–2.5 3.8–5.5 7.2–7.8(3H) 7.9–8.3(2H)

The percent of acyl groups in the compound to be calculated from the PMR data: 33%.

The percent of sulfate groups in the compound to be calculated from the elementary analysis value: 52%.

COMPOUND EXAMPLE 47

Synthesis of Sulfated dl-α-tocopheryl O-n-butyryl-β-D-laminari-heptaoside: (Compound 47)

dl-α-tocopheryl β-D-laminari-heptaoside was synthesized by using the similar method of REFERENCE SYNTHESES EXAMPLE 2.

Specific rotation of peracetyl dl-α-tocopheryl β-D-laminari-heptaoside: $[\alpha]_D=-45.9°$ (c=0.98/CHCl$_3$) (28° C.)

Specific rotation of dl-α-tocopheryl β-D-laminari-heptaoside: $[\alpha]_D=-36.5°$ (c=0.37/pyridine) (26° C.)

By using 24 mg of benzoyl chloride and 254 mg of sulfur trioxide pyridine complex, 131 mg of sulfated dl-α-tocopheryl O-n-butyryl-β-D-laminari-heptaoside was prepared from 73 mg of dl-α-tocopheryl β-D-laminari-heptaoside, in a manner similar to that for COMPOUND EXAMPLE 1.

Specific rotation: $[\alpha]_D=-18.8°$ (c=0.34/H$_2$O) (31° C.)

PMR spectra (D$_2$O) (ppm) 0.82–0.86(30.5H) 1.0–1.6 1.73(2H) 1.9–2.5 3.8–5.5

The percent of acyl groups in the compound to be calculated from the PMR data: 28%.

The percent of sulfate groups in the compound to be calculated from the elementary analysis value: 71%.

COMPOUND EXAMPLE 48

Synthesis of Sulfated dl-α-tocopheryl O-butyryl-β-D-maltotetraoside: (Compound 48)

dl-α-tocopheryl β-D-maltotetraoside was synthesized by using the similar method of REFERENCE SYNTHESES EXAMPLE 2.

Specific rotation of peracetyl dl-α-tocopheryl β-D-maltotetra-oside: $[\alpha]_D=+85.0°$ (c=0.48/CHCl$_3$) (26° C.)

Specific rotation of the dl-α-tocopheryl β-D-maltotetraoside: $[\alpha]_D=+87.6°$ (c=0.50/MeOH) (30° C.)

By using 320 mg of n-butyryl chloride and 1.76 g of sulfur trioxide pyridine complex, 984 mg of sulfated dl-α-tocopheryl O-n-butyryl-β-D-maltotetraoside was prepared from 829 mg of dl-α-tocopheryl β-D-maltotetraoside, in a manner similar to that for COMPOUND EXAMPLE 1.

Specific rotation: $[\alpha]_D=+41.7°$ (c=0.52/H$_2$O) (26° C.)

PMR spectra (DMSO-d$_6$) (ppm) 0.82–0.86(18.6H) 1.0–1.6 1.73(2H) 2.0–2.4 3.8–5.3

The percent of acyl groups in the compound to be calculated from the PMR data: 17%.

The percent of the sulfate groups in the compound to be calculated from the elementary analysis value: 71%.

EXAMPLE 49

Studies of Anti-HIV Activities of Compounds of the Present Invention

Method and results

A test compound having various concentrations were placed in a 96-well microtiter plate along with HIV-infected MT-4 cells (2.5×10$^4$/well, MOI (multiplicity of infection): 0.01) immediately after infection thereof. In order to ascertain the cytotoxicty of the test compound with respect to MT-4 cells, mock-infected (non-infected) cells were cultured in an identical manner along with the test compound of various concentrations. After incubating for 5 days at 37° C. in a CO$_2$ atmosphere, the number of living cells were determined by using MTT method. The anti-HIV activity was evaluated with the method written by R. Pauwels, et al. (R. Pauwels, et al., J. Virol Methods, 20, 309 to 321 (1988)).

The anti-HIV activity is shown in terms of EC$_{50}$ (50% effective concentration) that is the concentration of a compound which inhibits 50% of HIV-induced cytopathicity in MT-4 cells, and the cytotoxicity is shown in terms of CC$_{50}$ (cytotoxic concentration) that is the concentration of a compound which reduces 50% of viability of mock-infected MT-4 cells. Selectivity Index (S.I.) is expressed by the ratio of CC$_{50}$ to EC$_{50}$ (CC$_{50}$/EC$_{50}$). The results are shown in TABLE 1.

TABLE 1

| Compound No. | EC$_{50}$ (μg/ml) | CC$_{50}$ (μg/ml) | S.I. |
|---|---|---|---|
| 1 | 3.2 | 814 | 254 |
| 2 | 0.4 | >1,000 | >2,500 |
| 3 | 2.0 | 964 | 482 |
| 4 | 1.7 | 866 | 509 |
| 5 | 1.3 | 986 | 758 |
| 6 | 1.8 | >1,000 | >556 |
| 7 | 2.1 | >1,000 | >476 |
| 8 | 6.8 | 556 | 82 |
| 9 | 14.1 | 496 | 35 |
| 11 | 4.7 | 557 | 119 |
| 12 | 16.1 | 530 | 33 |
| 14 | 16.4 | 557 | 119 |
| 17 | 76.3 | 484 | 6 |
| 18 | 14.5 | 634 | 47 |
| 26 | 1.7 | >1,000 | >588 |
| 27 | 0.63 | >1,000 | >1,587 |
| 30 | 0.59 | 663 | 1,124 |
| 31 | 1.1 | 214 | 195 |
| 32 | 6.4 | 115 | 18 |
| 33 | 0.64 | 639 | 998 |
| 34 | 16.0 | 472 | 30 |
| 35 | 20.2 | 519 | 26 |
| 36 | 3.9 | 323 | 83 |
| 37 | 25.1 | 77.4 | 3 |
| 38 | 18.7 | 81.1 | 4 |
| 39 | 15.3 | 586 | 38 |
| 40 | 20.6 | 546 | 27 |
| 41 | 5.4 | 586 | 109 |
| 42 | 3.6 | 627 | 174 |
| 43 | 3.3 | 644 | 195 |
| 44 | 0.52 | 685 | 1,317 |
| 45 | 1.8 | 642 | 357 |
| 46 | 3.9 | 160 | 41 |

EXAMPLE 50

Intravenously Administered Mice Experiment

The effects of Compound 6 and dextran sulfate in vivo experiment were studied by duration of the activity using mouse.

1. The test substance

Compound 6 were dissolved with saline at the concentration of 32 mg/10 ml. Dextran sulfate (Control compound: M.W=8000: Sigma) were dissolved with it at the concentration of 80 mg/10 ml.

2. Animals

Mouse (Crj:CD-1(ICR)) (supplier: Charles River Japan, Inc.), six weeks old were used for this study.

3. Method and results

Four groups (for 1, 4, 6 and 12 hours) of mice (one group: three mice) were used for the in vivo experiments of the Compound 6.

The twelve mice were given an intravenous injection of the compound (in the tail vein; Dose 32 mg/kg).

Three groups (for 20, 40 and 60 minutes) of mice (one group: two mice) were used for dextran sulfate such a method as described in Compound 6 (Dose 80 mg/kg). At decided times after injection, the blood was collected and serum was separated by centrifugation at low speed.

The serum samples were stored at −80° C. until assayed. Each serum sample was diluted with culture medium to evaluate the effective concentration (the maximum concentration was set up to 10%). The method of this anti-HIV activity evaluation was the same one as described in EXAMPLE 49.

The result indicates that Compound 6 was detected at a high concentration, which is expressed with the reciprocal of the concentration of the serum, even twelve hours after injection (TABLE 2-1) and was proved to be effective on duration of the activity.

On the other hand, dextran sulfate could not be detected in the conditions of shorter time and higher dose than those of Compound 6 (TABLE 2-2).

TABLE 2-1

| | (Compound 6) |
|---|---|
| time after injection (hour) | reciprocal number(*) of concentration of the compound at 50% cell viability |
| 1 | 145 |
| 4 | 94 |
| 6 | 60 |
| 12 | 48 |

TABLE 2-2

| | (dextran sulfate) |
|---|---|
| time after injection (min) | reciprocal number(*) of concentration of dextran sulfate at 50% cell viability |
| 20 | <10 |
| 40 | <10 |
| 60 | <10 |

(*)Various concentration of the serum solutions (diluted with the medium and the maximum concentration is 10%) were used for evaluation of the concentration that exhibits $EC_{50}$ value of the serum. And the reciprocal number of the concentration that exhibits the $EC_{50}$ is shown. That is why the higher the reciprocal number, the higher the activity.

EXAMPLE 51

Orally Administered Mice Experiment

The effects of orally administration of Compound 1 in vivo experiment were studied by duration of the activity using mouse.
1. The test substance
   Compound 1 was dissolved with distilled water at the concentrations of 500 mg/10 ml and 1000 mg/10 ml.
2. Animals
   Mouse (Crj:CD-1(ICR)) (supplier: Charles River Japan, Inc.), six weeks old were used for this study.
3. Method and results
   Three groups (for 1, 2 and 3 hours) of mice (one group: three mice) were used for the in vivo experiments. Nine mice were given an orally administered of Compound 1 at a dose of 500 mg/kg or 1.0 g/kg.

At decided times after administration, the blood was collected and the serum was collected by centrifugation at low speed.

The serum samples were stored at −80° C. until assayed.

Each serum sample was diluted to evaluate the effective concentration with culture medium. The evaluation method was the same as described the section of Anti-HIV activity.

The result indicates that the compound was detected at a high concentration, which is expressed with the reciprocal of the concentration of the serum (TABLE 3) and was proved to be effective to orally administration. On the other hand, dextran sulfate was reported that it is poorly absorbed after oral administration by Kevin (Kevin J. Lorentsen et al., Annals of Internal Medicine, 111, 561 to 566(1989)).

TABLE 3

| time after orally administration (hour) | reciprocal number of concentration at 50% cell viability | |
|---|---|---|
| | 500 mg/kg | 1.0 g/kg |
| 1 | 15.9 | 55.6 |
| 2 | 19.2 | 83.8 |
| 3 | 26.7 | 54.1 |

EXAMPLE 52

Effects on Blood Clotting

The effects of Compound 1, 6 and dextran sulfate on blood clotting were studied by whole blood clotting time using rabbit blood.
1. The test substance
   Compound 1, 6 and dextran sulfate were dissolved with saline at the concentrations of 1, 0.1 and 0.01%. Sodium heparin (Kodama) used as positive control was diluted with saline at the concentration of 120 U/ml.
2. Animals
   Japan White rabbits (supplier: Kitayama Labes), 4 months old, were used for this study.
3. Method and results
   In advance, each 100 μl of Compound 1, 6 and dextran sulfate solutions of each concentration, sodium heparin solution or saline (negative control) were put in double glass tubes of 10 mm in diameter, and kept at 37° C. in a incubator. Cardiopuncture was performed in a rabbit, and at when blood was started to be flowed into the syringe, the timer was made to start. The whole blood collected was carefully flowed into double glass tubes incubated. After putting the samples calmly for 3 minutes, the first tube was tilted gently every 30 seconds and the current of blood was observed. When blood in the first tube was clotted, the same operation was performed in the second tube. When the blood was clotted in the second tube, the timer was stopped, and this end point was recorded as whole blood clotting time. The results are shown in TABLES 4-1 to 4-3.

Comparing strength of effects among Compound 1, 6 and dextran sulfate at the concentration of more than 0.1%, the results were as follow; dextran sulfate>1>6.

TABLE 4-1

| Compound | Concentration | clotting time (min) |
|---|---|---|
| Saline | — | 7.1 ± 0.4 |
| Compound 1 | 0.01% | 8.0 ± 0.5 |
|  | 0.1% | 8.3 ± 0.7 |
|  | 1.0% | 27.3 ± 3.0 |
| Heparin | 120 U/ml | >60 |

TABLE 4-2

| Compound | Concentration | clotting time (min) |
|---|---|---|
| Saline | — | 7.4 ± 0.6 |
| Compound 6 | 0.01% | 7.4 ± 0.6 |
|  | 0.1% | 7.4 ± 0.6 |
|  | 1.0% | 21.1 ± 1.7 |
| Heparin | 120 U/ml | >60 |

TABLE 4-3

| Compound | Concentration | clotting time (min) |
|---|---|---|
| Saline | — | 7.1 ± 0.5 |
| Dextran sulfate | 0.01% | 7.7 ± 0.5 |
|  | 0.1% | 42.4 ± 3.6 |
|  | 1.0% | >60 |
| Heparin | 120 U/ml | >60 |

ANTIVIRAL AGENT PRODUCTION EXAMPLE 1

| | |
|---|---|
| Compound 1 | 50 mg |
| Starch | 30 mg |
| Lactose | 110 mg |
| Talc | 7 mg |
| Magnesium stearate | 3 mg |
| | 200 mg |

Compound 1 was ground and mixed together with lactose and starch. Then, 10% of starch paste was added to the above mixture, which was stirred until granules were formed. The granules were dried and sieved, talc and magnesium stearate were added, and the mixture was processed by the ordinary method to prepare the 200 mg tablet.

ANTIVIRAL AGENT PRODUCTION EXAMPLE 2

| | |
|---|---|
| Compound 2 | 50 mg |
| Starch | 30 mg |
| Lactose | 110 mg |
| Talc | 7 mg |
| Magnesium stearate | 3 mg |
| | 200 mg |

The same procedure as used in ANTIVIRAL AGENT PRODUCTION EXAMPLE 1 was repeated for Compound 2 to prepare the 200 mg tablet.

ANTIVIRAL AGENT PRODUCTION EXAMPLE 3

| | |
|---|---|
| Compound 3 | 50 mg |
| Starch | 30 mg |
| Lactose | 110 mg |
| Talc | 7 mg |
| Magnesium stearate | 3 mg |
| | 200 mg |

The same procedure as used in ANTIVIRAL AGENT PRODUCTION EXAMPLE 1 was repeated for Compound 3 to prepare the 200 mg tablet.

ANTIVIRAL AGENT PRODUCTION EXAMPLE 4

| | |
|---|---|
| Compound 4 | 50 mg |
| Starch | 30 mg |
| Lactose | 110 mg |
| Talc | 7 mg |
| Magnesium stearate | 3 mg |
| | 200 mg |

The same procedure as used in ANTIVIRAL AGENT PRODUCTION EXAMPLE 1 was repeated for Compound 4 to prepare the 200 mg tablet.

ANTIVIRAL AGENT PRODUCTION EXAMPLE 5

| | |
|---|---|
| Compound 5 | 50 mg |
| Starch | 30 mg |
| Lactose | 110 mg |
| Talc | 7 mg |
| Magnesium stearate | 3 mg |
| | 200 mg |

The same procedure as used in ANTIVIRAL AGENT PRODUCTION EXAMPLE 1 was repeated for Compound 5 to prepare the 200 mg tablet.

ANTIVIRAL AGENT PRODUCTION EXAMPLE 6

| | |
|---|---|
| Compound 6 | 50 mg |
| Starch | 30 mg |
| Lactose | 110 mg |
| Talc | 7 mg |
| Magnesium stearate | 3 mg |
| | 200 mg |

The same procedure as used in ANTIVIRAL AGENT PRODUCTION EXAMPLE 1 was repeated for Compound 6 to prepare the 200 mg tablet.

ANTIVIRAL AGENT PRODUCTION EXAMPLE 7

| | |
|---|---|
| Compound 7 | 25 mg |
| Lactose | 50 mg |
| Starch | 23 mg |
| Magnesium stearate | 2 mg |
| | 100 mg |

Compound 7 was ground and mixed together with lactose and starch. Then, 10% of starch paste was added to the above mixture, which was stirred until granules were formed. The granules were dried and sieved, magnesium stearate were added, and the mixture was processed by the ordinary method to prepare the 100 mg tablet.

ANTIVIRAL AGENT PRODUCTION EXAMPLE 8

| | |
|---|---|
| Compound 27 | 50 mg |
| Starch | 30 mg |
| Lactose | 10 mg |
| Talc | 7 mg |
| Magnesium stearate | 3 mg |
| | 200 mg |

The same procedure used in ANTIVIRAL AGENT PRODUCTION EXAMPLE 1 was repeated for Compound 27 to prepare the 200 mg tablet.

ANTIVIRAL AGENT PRODUCTION EXAMPLE 9

| | |
|---|---|
| Compound 31 | 50 mg |
| Starch | 30 mg |
| Lactose | 110 mg |
| Talc | 7 mg |
| Magnesium stearate | 3 mg |
| | 200 mg |

The same procedure used in ANTIVIRAL AGENT PRODUCTION EXAMPLE 1 was repeated for Compound 31 to prepare the 200 mg tablet.

ANTIVIRAL AGENT PRODUCTION EXAMPLE 10

| | |
|---|---|
| Compound 42 | 50 mg |
| Starch | 30 mg |
| Lactose | 110 mg |
| Talc | 7 mg |
| Magnesium stearate | 3 mg |
| | 200 mg |

The same procedure used in ANTIVIRAL AGENT PRODUCTION EXAMPLE 1 was repeated for Compound 42 to prepare the 200 mg tablet.

ANTIVIRAL AGENT PRODUCTION EXAMPLE 11

| | |
|---|---|
| Compound 47 | 50 mg |
| Starch | 30 mg |
| Lactose | 110 mg |
| Talc | 7 mg |
| Magnesium stearate | 3 mg |
| | 200 mg |

The same procedure used in ANTIVIRAL AGENT PRODUCTION EXAMPLE 1 was repeated for Compound 47 to prepare the 200 mg tablet.

ANTIVIRAL AGENT PRODUCTION EXAMPLE 12

| | |
|---|---|
| Compound 48 | 50 mg |
| Starch | 30 mg |
| Lactose | 110 mg |
| Talc | 7 mg |
| Magnesium stearate | 3 mg |
| | 200 mg |

The same procedure used in ANTIVIRAL AGENT PRODUCTION EXAMPLE 1 was repeated for Compound 48 to prepare the 200 mg tablet.

ANTIVIRAL AGENT PRODUCTION EXAMPLE 13

Physiological saline solution was added to 500 mg of compound 1, to a total volume of 10 ml to dissolve the compound therein. The mixture was then transferred into an ampule that had been sterilized by an auto-clave, to prepare 10 ml of the medicine.

ANTIVIRAL AGENT PRODUCTION EXAMPLE 14

Physiological saline solution was added to 500 mg of compound 2 to prepare 10 ml of the medicine using the same procedure as used for ANTIVIRAL AGENT PRODUCTION EXAMPLE 13.

ANTIVIRAL AGENT PRODUCTION EXAMPLE 15

Physiological saline solution was added to 600 mg of Compound 3 to prepare 10 ml of the medicine using the same procedure as used for ANTIVIRAL AGENT PRODUCTION EXAMPLE 13.

ANTIVIRAL AGENT PRODUCTION EXAMPLE 16

Physiological saline solution was added to 600 mg of Compound 4 to prepare 10 ml of the medicine using the same procedure as used for ANTIVIRAL AGENT PRODUCTION EXAMPLE 13.

ANTIVIRAL AGENT PRODUCTION EXAMPLE 17

Physiological saline solution was added to 600 mg of Compound 5 to prepare 10 ml of the medicine using the same procedure as used for ANTIVIRAL AGENT PRODUCTION EXAMPLE 13.

ANTIVIRAL AGENT PRODUCTION EXAMPLE 18

Physiological saline solution was added to 500 mg of Compound 6 to prepare 10 ml of the medicine using the same procedure as used for ANTIVIRAL AGENT PRODUCTION EXAMPLE 13.

ANTIVIRAL AGENT PRODUCTION EXAMPLE 19

Physiological saline solution was added to 500 mg of Compound 7 to prepare 10 ml of the medicine using the same procedure as used for ANTIVIRAL AGENT PRODUCTION EXAMPLE 13.

ANTIVIRAL AGENT PRODUCTION EXAMPLE 20

Physiological saline solution was added to 500 mg of Compound 24 to prepare 10 ml of the medicine using the same procedure as used for ANTIVIRAL AGENT PRODUCTION EXAMPLE 13.

ANTIVIRAL AGENT PRODUCTION EXAMPLE 21

Physiological saline solution was added to 500 mg of Compound 47 to prepare 10 ml of the medicine using the same procedure as used for ANTIVIRAL AGENT PRODUCTION EXAMPLE 13.

ANTIVIRAL AGENT PRODUCTION EXAMPLE 22

500 mg of compound 1 was ground and mixed together with 1000 mg of mannitol and 400 mg of disodium phosphate. Then, the above mixture was added to an ampule, which had been sterilized by an auto-clave.

The ampule was sealed to prepare a medicine.

ANTIVIRAL AGENT PRODUCTION EXAMPLE 23

500 mg of compound 2 was ground and mixed together with 1000 mg of mannitol and 400 mg of disodium phosphate. Then, the above mixture was added to an ampule, which had been sterilized by an auto-clave.

The ampule was sealed to prepare a medicine.

ANTIVIRAL AGENT PRODUCTION EXAMPLE 24

500 mg of compound 3 was ground and mixed together with 1000 mg of mannitol and 400 mg of disodium phosphate. Then, the above mixture was added to an ampule, which had been sterilized by an auto-clave.

The ampule was sealed to prepare a medicine.

ANTIVIRAL AGENT PRODUCTION EXAMPLE 25

500 mg of compound 4 was ground and mixed together with 1000 mg of mannitol and 400 mg of disodium phosphate. Then, the above mixture was added to an ampule, which had been sterilized by an auto-clave.

The ampule was sealed to prepare a medicine.

ANTIVIRAL AGENT PRODUCTION EXAMPLE 26

500 mg of compound 5 was ground and mixed together with 1000 mg of mannitol and 400 mg of disodium phosphate. Then, the above mixture was added to an ampule, which had been sterilized by an auto-clave.

The ampule was sealed to prepare a medicine.

ANTIVIRAL AGENT PRODUCTION EXAMPLE 27

500 mg of compound 20 was ground and mixed together with 1000 mg of mannitol and 400 mg of disodium phosphate. Then, the above mixture was added to an ampule, which had been sterilized by an auto-clave.

The ampule was sealed to prepare a medicine.

While the invention has been described in detail and with reference to specific examples thereof, it will be apparent to one skilled in the art that various changes and modificaitons can be made therein without departing from the spirit and scope thereof.

What is claimed is:

1. A sulfated oligoglycoside acylate wherein the saccharides comprising the oligosaccharide moiety are selected from the group consisting of β(1–3)-glucose saccharides, β(1–4)-galactose saccharides, α(1–4)-glucose saccharides, β(1–4)-lactose saccharides and mixtures of these saccharides, wherein the hydrogen in the hydroxyl group at the 1-position of a reducing end sugar of the oligosaccharide formed via the glycoside bond of these saccharides has been substituted with an aglycon selected from the group consisting of $C_1$–$C_{24}$ alkyl groups, $C_1$–$C_{18}$ alkyl phenyl groups, $C_1$–$C_{18}$ alkoxy phenyl groups, and tocopheryl groups; from 12 to 80% of the residual hydroxyl groups have been acylated with an acyl group selected from the group consisting of aliphatic acyl groups having 2 to 24 carbon atoms, an unsubstituted benzoyl group and a benzoyl group substituted with an alkyl group, or an alkoxy group or a halogen atom; and from 88 to 20% thereof have been sulfated; or a physiologically acceptable salt thereof; with the proviso that the compounds do not simultaneously have an alkyl group as the aglycon and an aliphatic acyl group as the acyl group.

2. The sulfated oligoglycoside acylate or a physiologically acceptable salt thereof as claimed in claim 1 wherein said oligosaccharide moiety is an oligosaccharide consisting of 3 to 20 monosaccharides of a single kind of monosaccharide.

3. The sulfated oligoglycoside acylate or a physiologically acceptable salt thereof as claimed in claim 1 wherein said oligosaccharide moiety is an oligosaccharide formed by a β(1–3)-glucose.

4. The sulfated oligoglycoside acylate or a physiologically acceptable salt thereof as claimed in claim 1 wherein said oligosaccharide moiety is an oligosaccharide formed by an α(1–4)-glucose.

5. The sulfated oligoglycoside acylate or a physiologically acceptable salt thereof as claimed in claim 1 wherein the oligosaccharide moiety is a mixture of saccharides and contains 3 to 20 monosaccharides.

6. The sulfated oligoglycoside acylate or a physiologically acceptable salt thereof as claimed in claim 5 wherein said oligosaccharide moiety is an oligosaccharide formed by a β(1–4)bond.

7. The sulfated oligoglycoside acylate or a physiologically acceptable salt thereof as claimed in claim 1 wherein said aglycon is a straight-chain or branched alkyl group having 4 to 22 carbon atoms and said acyl group is an aromatic acyl group selected from the group consisting of an unsubstituted benzoyl group and a benzoyl group substituted with a $C_1$–$C_{18}$ alkyl group, or a $C_1$–$C_{18}$ alkoxy group, or a halogen atom.

8. The sulfated oligoglycoside acylate or a physiologically acceptable salt thereof as claimed in claim 7 wherein said acyl group is an aromatic acyl group selected from the group consisting of an unsubstituted benzoyl group and a benzoyl group substituted with a $C_3$–$C_{12}$ alkyl group or a $C_3$–$C_{12}$ alkoxy group, or a fluorine.

9. The sulfated oligoglycoside acylate or a physiologically acceptable salt thereof as claimed in claim 1 wherein said aglycon is a phenyl group substituted with a straight-chain or branched alkyl group having 4 to 12 carbon atoms and said acyl group is an acyl group selected from the group consisting of aliphatic acyl groups having 2 to 24 carbon atoms, an unsubstituted benzoyl group and a benzoyl group substituted with a $C_1$–$C_{18}$ alkyl group, or a $C_1$–$C_{18}$ alkoxy group, or a halogen atom.

10. The sulfated oligoglycoside acylate or a physiologically acceptable salt thereof as claimed in claim 9 wherein said acyl group is a straight-chain or branched alkanoyl group having 3 to 22 carbon atoms.

11. The sulfated oligoglycoside acylate or a physiologically acceptable salt thereof as claimed in claim 9 wherein said acyl group is an aromatic acyl group selected from the group consisting of an unsubstituted benzoyl group and a benzoyl group substituted with a $C_3$–$C_{12}$ alkyl group, or a $C_3$–$C_{12}$ alkoxy group, or a fluorine.

12. The sulfated oligoglycoside acylate or a physiologically acceptable salt thereof as claimed in claim 1 wherein said aglycon is a phenyl group substituted with a straight-chain or branched alkoxy group having 4 to 12 carbon atoms and said acyl group is an acyl group selected from the group consisting of aliphatic acyl group having 2 to 24 carbon atoms, an unsubstituted benzoyl group and a benzoyl group substituted with a $C_1$–$C_{18}$ alkyl group, or a $C_1$–$C_{18}$ alkoxy group, or a halogen atom.

13. The sulfated oligoglycoside acylate or a physiologically acceptable salt thereof as claimed in claim 12 wherein said acyl group is a straight-chain or branched alkanoyl group having 3 to 22 carbon atoms.

14. The sulfated oligoglycoside acylate or a physiologically acceptable salt thereof as claimed in claim 12 wherein said acyl group is an aromatic acyl group selected from a group consisting of an unsubstituted benzoyl group and a benzoyl group substituted with a $C_3$–$C_{12}$ alkyl group, or a $C_3$–$C_{12}$ alkoxy group, or a fluorine.

15. The sulfated oligoglycoside acylate or a physiologically acceptable salt thereof as claimed in claim 1 wherein said aglycon is a tocopheryl group and said acyl group is an acyl group selected from a group consisting of aliphatic acyl groups having 2 to 24 carbon atoms, an unsubstituted benzoyl group and a benzoyl group substituted with a $C_1$–$C_{18}$ alkyl group or a $C_1$–$C_{18}$ alkoxy group, or a halogen atom.

16. The sulfated oligoglycoside acylate or a physiologically acceptable salt thereof as claimed in claim 15 wherein said acyl group is a straight-chain or branched alkanoyl group having 3 to 22 carbon atoms.

17. The sulfated oligoglycoside acylate or a physiologically acceptable salt thereof as claimed in claim 15 wherein said acyl group is an aromatic acyl group selected from a group consisting of an unsubstituted benzoyl group and a benzoyl group substituted with a $C_3$–$C_{12}$ alkyl group, or a $C_3$–$C_{12}$ alkoxy group or a fluorine.

18. A pharmaceutical composition comprising a sulfated oligoglycoside acylate or physiologically acceptable salt thereof as claimed in claim 1 in combination with a pharmaceutically acceptable carrier.

19. A method for the treatment of diseases induced by HIV which comprises the administration of an effective amount of the sulfated oligoglycoside acylate as recited in claim 1 or a physiologically acceptable salt thereof.

20. A sulfated oligoglycoside acylate wherein the saccharides comprising the oligosaccharide moiety are selected from the group consisting of β(1–3)-glucose saccharides, β(1–4)-galactose saccharides, α(1–4)-glucose saccharides, β(1–4)-lactose saccharides and mixtures of these saccharides, wherein the hydrogen in the hydroxyl group at the 1-position of a reducing end sugar of the oligosaccharides formed via the glycoside bond of these saccharides has been substituted with an aglycon selected from the group consisting of $C_8$–$C_{18}$ alkyl groups, $C_4$–$C_{12}$ alkyl phenyl groups, $C_4$–$C_{12}$ alkoxy phenyl groups, and tocopheryl groups; from 12 to 80% of the residual hydroxyl groups have been acylated with an acyl group selected from the group consisting of aliphatic acyl groups having 3 to 22 carbon atoms, an unsubstituted benzoyl group and a benzoyl group substituted with a $C_1$–$C_5$ alkyl group, or a $C_1$–$C_4$ alkoxy group, or a fluorine; and from 88 to 20% thereof have been sulfated; or a physiologically acceptable salt thereof; with the proviso that the compounds do not simultaneously have an alkyl group as the aglycon and an aliphatic acyl group as the acyl group.

21. The sulfated oligoglycoside acylate or a physiologically acceptable salt thereof as claimed in claim 6 wherein said oligosaccharide moiety is an oligosaccharide wherein the 4-position of the galactose site in lactose forms a β-bond together with the 1-position of galactose and galactose units subsequently from β(1–4) bonds together with the 4-position of the terminal galactose of oligosaccharide.

* * * * *